US012564552B2

(12) United States Patent
Zawadzki et al.

(10) Patent No.: US 12,564,552 B2
(45) Date of Patent: Mar. 3, 2026

(54) ORAL PRODUCT WITH A BASIC AMINE AND AN ION PAIRING AGENT

(71) Applicant: NICOVENTURES TRADING LIMITED, London (GB)

(72) Inventors: Michael Zawadzki, Clemmons, NC (US); Kai Tang, London (GB); Steven Lee Alderman, Lewisville, NC (US); Thomas H. Poole, Winston-Salem, NC (US)

(73) Assignee: NICOVENTURES TRADING LIMITED, London (GB)

( * ) Notice: Subject to any disclaimer, the term of this patent is extended or adjusted under 35 U.S.C. 154(b) by 0 days.

(21) Appl. No.: 17/955,895

(22) Filed: Sep. 29, 2022

(65) Prior Publication Data

US 2023/0138306 A1 May 4, 2023

Related U.S. Application Data

(60) Provisional application No. 63/250,631, filed on Sep. 30, 2021.

(51) Int. Cl.
*A61K 31/194* (2006.01)
*A61K 9/00* (2006.01)
(Continued)

(52) U.S. Cl.
CPC .......... *A61K 9/0053* (2013.01); *A61K 31/194* (2013.01); *A61K 31/4439* (2013.01); *A61K 45/06* (2013.01); *A61K 47/38* (2013.01)

(58) Field of Classification Search
CPC ................ A61K 9/0053; A61K 31/194; A61K 31/4439; A61K 45/06; A61K 47/38
See application file for complete search history.

(56) References Cited

U.S. PATENT DOCUMENTS 5,417,229 A 5/1995 Summers et al.
5,725,865 A * 3/1998 Mane .................... A23L 27/203 514/774

(Continued)

FOREIGN PATENT DOCUMENTS

CN 103005680 4/2013
CN 103263507 8/2013

(Continued)

OTHER PUBLICATIONS

Hiserodt et al. J. Agric. Food Chem. 2004, 52, 11, 3536-3541. (Year: 2004).*

(Continued)

*Primary Examiner* — Joseph K McKane
*Assistant Examiner* — Ashli Ariana Chicks
(74) *Attorney, Agent, or Firm* — Womble Bond Dickinson (US) LLP; Scott R. Breining

(57) ABSTRACT

The disclosure provides a composition configured for oral use, the composition including at least one filler, water, a basic amine, and an organic acid, an alkali metal salt of an organic acid, or a combination thereof, wherein the organic acid has a log P value of from about 1 to about 12. At least a portion of the basic amine is associated with at least a portion of the organic acid or the alkali metal salt thereof. The association is in the form of a basic amine-organic acid salt, an ion pair between the basic amine and a conjugate base of the organic acid, or a combination of both. The organic acid is a monoester of a dicarboxylic acid or is a carotenoid derivative having one or more carboxylic acids.

25 Claims, 1 Drawing Sheet

(51) Int. Cl.
*A61K 31/4439* (2006.01)
*A61K 45/06* (2006.01)
*A61K 47/38* (2006.01)

(56) References Cited

U.S. PATENT DOCUMENTS 6,138,683 A 10/2000 Hersh et al.
6,845,777 B2 1/2005 Pera
6,958,143 B2 10/2005 Choi et al.
7,032,601 B2 4/2006 Atchley et al.
7,056,541 B1 6/2006 Stahl et al.
7,507,427 B2 3/2009 Andersen et al.
7,810,507 B2 10/2010 Dube et al.
7,833,555 B2 11/2010 Andersen et al.
7,861,728 B2 1/2011 Holton, Jr. et al.
7,900,637 B2 3/2011 Fagerstrom et al.
7,950,399 B2 5/2011 Winterson et al.
8,069,861 B2 12/2011 Sinclair, Jr.
8,124,147 B2 2/2012 Cheng et al.
8,293,295 B2 10/2012 Andersen et al.
8,336,557 B2 12/2012 Kumar et al.
8,343,532 B2 1/2013 Dam et al.
8,424,541 B2 4/2013 Crawford et al.
8,469,036 B2 6/2013 Williams et al.
8,469,037 B2 6/2013 Liu et al.
8,529,875 B2 9/2013 Andersen
8,529,914 B2 9/2013 Fuisz et al.
8,545,870 B2 10/2013 Dupinay et al.
8,591,967 B2 11/2013 Andersen et al.
8,613,285 B2 12/2013 Fuisz
8,627,828 B2 1/2014 Strickland et al.
8,642,016 B2 2/2014 Chau et al.
8,714,163 B2 5/2014 Kumar et al.
8,741,348 B2 6/2014 Hansson et al.
8,747,562 B2 6/2014 Mishra et al.
8,828,361 B2 9/2014 Andersen
8,833,378 B2 9/2014 Axelsson et al.
8,846,075 B2 9/2014 Johnson et al.
8,858,984 B2 10/2014 Dam et al.
8,863,755 B2 10/2014 Zhuang et al.
8,871,243 B2 10/2014 Fankhauser et al.
8,931,493 B2 1/2015 Sebastian et al.
8,945,593 B2 2/2015 LoCoco et al.
8,978,661 B2 3/2015 Atchley et al.
8,992,974 B2 3/2015 McCarty
9,027,567 B2 5/2015 Gee et al.
9,039,839 B2 5/2015 Beeson et al.
9,044,035 B2 6/2015 Jackson et al.
9,084,439 B2 7/2015 Holton, Jr.
9,155,321 B2 10/2015 Cantrell et al.
9,161,567 B2 10/2015 Shikata et al.
9,161,908 B2 10/2015 Nilsson
9,167,835 B2 10/2015 Sengupta et al.
9,185,931 B2 11/2015 Gao et al.
9,204,667 B2 12/2015 Cantrell et al.
9,237,768 B2 1/2016 Carroll et al.
9,358,296 B2 6/2016 McCarty
9,372,033 B2 6/2016 Lampe et al.
9,386,800 B2 7/2016 Sebastian et al.
9,402,414 B2 8/2016 Griscik et al.
9,402,809 B2 8/2016 Axelsson et al.
9,414,624 B2 8/2016 Carroll et al.
9,420,825 B2 8/2016 Beeson et al.
9,468,233 B2 10/2016 Macko et al.
9,474,303 B2 10/2016 Holton, Jr.
9,521,864 B2 12/2016 Gao et al.
9,565,867 B2 2/2017 Wittorff et al.
9,629,392 B2 4/2017 Holton, Jr.
9,635,881 B2 5/2017 Sjögren et al.
9,675,102 B2 6/2017 Hunt et al.
9,763,928 B2 9/2017 Duggins et al.
9,775,376 B2 10/2017 Cantrell et al.
9,801,409 B1 10/2017 Smith
9,848,634 B2 12/2017 Fuisz
9,854,830 B2 1/2018 Gao et al.
9,884,015 B2 2/2018 Gao et al.
9,907,748 B2 3/2018 Borschke et al.
9,925,145 B2 3/2018 Hubinette et al.
9,930,909 B2 4/2018 Gao et al.
9,999,243 B2 6/2018 Gao et al.
10,039,309 B2 8/2018 Carroll et al.
10,045,976 B2 8/2018 Fusco et al.
10,092,715 B2 10/2018 Axelsson et al.
10,130,120 B2 11/2018 Mishra et al.
10,143,230 B2 12/2018 Mishra et al.
10,149,850 B2 12/2018 Mishra et al.
10,172,810 B2 1/2019 McCarty
10,244,786 B2 4/2019 Gao et al.
10,334,873 B2 7/2019 Mishra et al.
10,357,054 B2 7/2019 Marshall et al.
10,375,984 B2 8/2019 Hernandez Garcia et al.
10,390,557 B2 8/2019 Börjesson et al.
10,426,726 B2 10/2019 Neergaard
10,463,070 B2 11/2019 Carroll et al.
10,532,046 B2 1/2020 Rogers et al.
10,543,205 B2 1/2020 Wittorff et al.
2004/0118422 A1 6/2004 Lundin et al.
2007/0031539 A1 2/2007 Calton
2008/0081071 A1 4/2008 Sanghvi et al.
2008/0166395 A1* 7/2008 Roush .................. A61K 9/0056
514/343
2009/0023819 A1 1/2009 Axelsson
2009/0065013 A1 3/2009 Essen et al.
2009/0253754 A1 10/2009 Selmin et al.
2009/0301504 A1 12/2009 Worthen et al.
2010/0004294 A1 1/2010 Axelsson et al.
2010/0061940 A1 3/2010 Axelsson et al.
2010/0187143 A1 7/2010 Essen et al.
2010/0260690 A1 10/2010 Kristensen et al.
2010/0294292 A1 11/2010 Hodin et al.
2011/0139164 A1 6/2011 Mua et al.
2011/0220130 A1 9/2011 Mua et al.
2011/0268809 A1 11/2011 Brinkley et al.
2012/0031415 A1 2/2012 Essen et al.
2012/0037175 A1 2/2012 Cantrell et al.
2013/0078307 A1 3/2013 Holton, Jr. et al.
2013/0118512 A1 5/2013 Jackson et al.
2013/0152953 A1 6/2013 Mua et al.
2013/0177646 A1 7/2013 Hugerth et al.
2013/0206150 A1 8/2013 Duggins et al.
2013/0251779 A1 9/2013 Svandal et al.
2013/0340773 A1 12/2013 Sebastian et al.
2014/0130813 A1 5/2014 Strehle
2014/0154301 A1 6/2014 Chau et al.
2014/0255452 A1 9/2014 Reddick et al.
2014/0264992 A1 9/2014 Miller et al.
2014/0345635 A1* 11/2014 Rabinowitz .......... A24B 15/167
131/352
2015/0068544 A1 3/2015 Moldoveanu et al.
2015/0068545 A1 3/2015 Moldoveanu et al.
2015/0071972 A1 3/2015 Holton, Jr. et al.
2015/0096573 A1 4/2015 Gao et al.
2015/0096574 A1 4/2015 Gao et al.
2015/0096576 A1 4/2015 Gao et al.
2015/0296868 A1 10/2015 Sutton
2016/0000140 A1 1/2016 Sebastian et al.
2016/0073676 A1 3/2016 Cantrell et al.
2016/0073689 A1 3/2016 Sebastian et al.
2016/0157515 A1 6/2016 Chapman et al.
2016/0192703 A1 7/2016 Sebastian et al.
2017/0007594 A1 1/2017 Borschke
2017/0164651 A1 6/2017 Mua et al.
2017/0165252 A1 6/2017 Mua et al.
2017/0172995 A1 6/2017 Repaka et al.
2017/0280764 A1 10/2017 Sahlen et al.
2017/0312261 A1 11/2017 Changoer et al.
2017/0318858 A1 11/2017 Hodin et al.
2018/0140007 A1 5/2018 Aspgren et al.
2018/0140521 A1 5/2018 Geonnotti et al.
2018/0140554 A1 5/2018 Wittorff
2018/0153211 A1 6/2018 Persson
2018/0235273 A1 8/2018 Carroll et al.
2018/0255826 A1 9/2018 Persson et al.
2018/0257801 A1 9/2018 Persson

(56) References Cited

U.S. PATENT DOCUMENTS

| | | | |
|---|---|---|---|
| 2019/0037909 A1 | 2/2019 | Greenbaum et al. | |
| 2019/0174812 A1 | 6/2019 | Nielsen et al. | |
| 2019/0175581 A1 | 6/2019 | Nielsen et al. | |
| 2019/0255035 A1 | 8/2019 | Bruun | |
| 2019/0261672 A1* | 8/2019 | Chaparro Leal | C07D 401/04 |
| 2020/0037638 A1 | 2/2020 | Faraci et al. | |
| 2020/0128870 A1 | 4/2020 | Hassler et al. | |
| 2020/0138706 A1 | 5/2020 | Rudraraju et al. | |
| 2020/0275689 A1 | 9/2020 | Lewerenz | |
| 2020/0297026 A1 | 9/2020 | Kannisto et al. | |
| 2020/0305496 A1 | 10/2020 | Gessesse | |
| 2020/0383372 A1 | 12/2020 | Stahl et al. | |
| 2020/0383373 A1 | 12/2020 | Stahl et al. | |
| 2021/0068447 A1 | 3/2021 | Keller et al. | |
| 2021/0106516 A1 | 4/2021 | Nielsen | |
| 2021/0169122 A1 | 6/2021 | St. Charles | |
| 2021/0169126 A1 | 6/2021 | Keller et al. | |
| 2021/0169788 A1 | 6/2021 | Mua et al. | |

FOREIGN PATENT DOCUMENTS

| | | | |
|---|---|---|---|
| CN | 103494324 | 1/2014 | |
| CN | 105192876 | 12/2015 | |
| CN | 105595404 | 5/2016 | |
| CN | 110150760 | 8/2019 | |
| WO | WO 1996/031255 | 10/1996 | |
| WO | WO-2004075877 A1 * | 9/2004 | A61P 37/08 |
| WO | WO 2004/095959 | 11/2004 | |
| WO | WO 2005/041699 | 5/2005 | |
| WO | WO 2005/063060 | 5/2005 | |
| WO | WO 2008/103935 | 8/2008 | |
| WO | WO 2010/132444 | 11/2010 | |
| WO | WO 2017/089931 | 6/2017 | |
| WO | WO 2018/083114 | 5/2018 | |
| WO | WO-2019005889 A1 * | 1/2019 | A24B 13/00 |
| WO | WO 2019/036243 | 2/2019 | |
| WO | WO-2021225509 A1 * | 11/2021 | A24B 13/00 |

OTHER PUBLICATIONS

Viera-Herrera et al. Nanomaterials (Basel). 2020; 10(5):975. (Year: 2020).*

National Center for Biotechnology Information (PubChem Compound Summary for CID 10199004, Monomenthyl succinate. https://pubchem.ncbi.nlm.nih.gov/compound/Monomenthyl-succinate. Accessed Jan. 24, 2024. (Year: 2024).*

Gholap et al. Expert Opin Drug Deliv. Dec. 2020 ; 17(12): 1727-1736. (Year: 2020).*

Perfetti et al. (2000). The Transfer of Nicotine From Nicotine Salts to Mainstream Smoke. Beitrage zur Tabakforschung International / Contributions to Tobacco Research. 19. 141-158. (Year: 2000).*

Adrian et al., "In vivo human buccal permeability of nicotine" *International Journal of Pharmaceutics* 2006, 311, 196-202.

Chen et al., "A mechanistic analysis to characterize oramucosal permeation properties" *International Journal of Pharmaceutics* 1999, 184, 63-72.

Kokate et al., "Effect of Drug Lipophilicity and Ionization on Permeability Across the Buccal Mucosa: A Technical Note" *AAPPS PharmSciTech* 2008, 9, 501-504.

Nair et al., "Biomembrane Permeation of Nicotine: Mechanistic Studies with Porcine Mucosae and Skin" *Journal of Pharmaceutical Sciences* 1997, 86, 257-262.

Robichaud, Meagan et al., "Tobacco companies introduce 'tobacco free' nicotine pouches", *Tob Control* 2019, Nov. 21, 2019, 1-2, National Library of Medicine, doi:10.1136/tobaccocontrol-2019-055321.

* cited by examiner

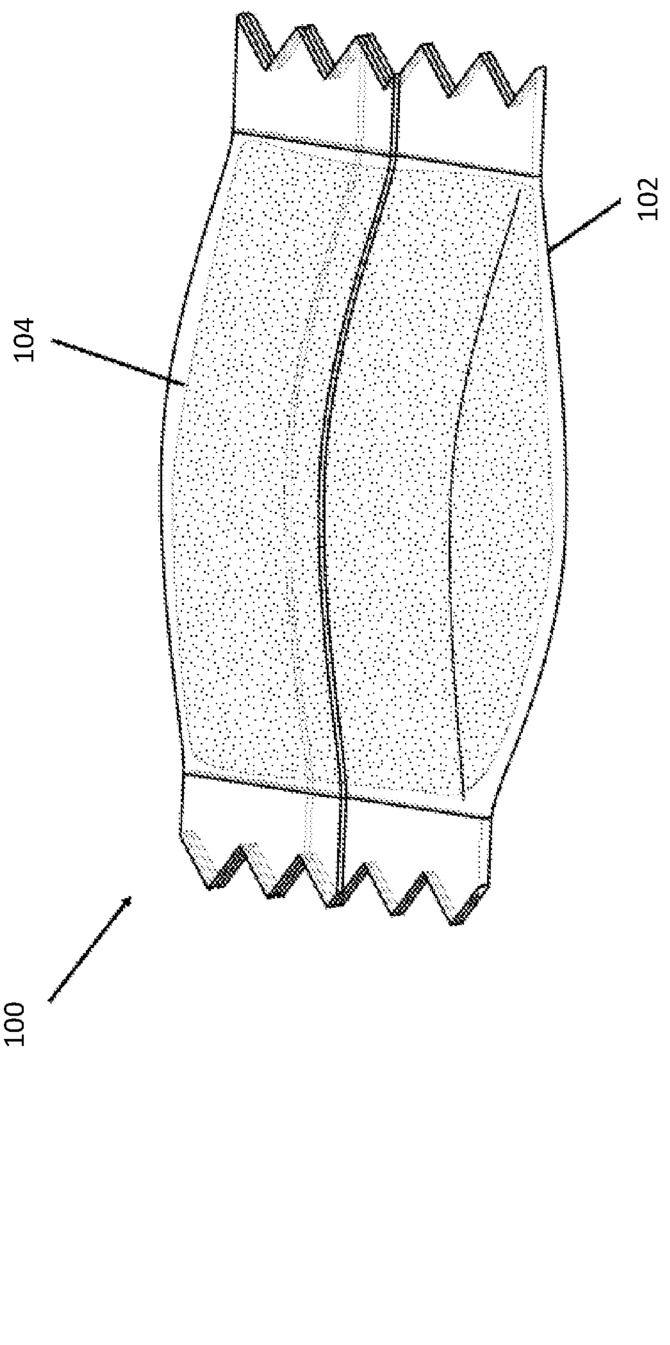
102
104
100

ORAL PRODUCT WITH A BASIC AMINE AND AN ION PAIRING AGENT

CROSS-REFERENCE TO RELATED APPLICATIONS

This application claims priority to U.S. Provisional Application No. 63/250,631, filed on Sep. 30, 2022, which is incorporated herein by reference in its entirety and for all purposes.

FIELD OF THE DISCLOSURE

The present disclosure relates to compositions intended for human use. The compositions are adapted for oral use and deliver substances such as nicotine, flavors, and/or active ingredients during use. Such compositions may include tobacco or a product derived from tobacco, or may be tobacco-free alternatives.

BACKGROUND

Tobacco may be enjoyed in a so-called “smokeless” form. Particularly popular smokeless tobacco products are employed by inserting some form of processed tobacco or tobacco-containing formulation into the mouth of the user. Conventional formats for such smokeless tobacco products include moist snuff, snus, and chewing tobacco, which are typically formed almost entirely of particulate, granular, or shredded tobacco, and which are either portioned by the user or presented to the user in individual portions, such as in single-use pouches or sachets. Other traditional forms of smokeless products include compressed or agglomerated forms, such as plugs, tablets, or pellets. Alternative product formats, such as tobacco-containing gums and mixtures of tobacco with other plant materials, are also known.

See for example, the types of smokeless tobacco formulations, ingredients, and processing methodologies set forth in U.S. Pat. No. 1,376,586 to Schwartz; U.S. Pat. No. 4,513,756 to Pittman et al.; U.S. Pat. No. 4,528,993 to Sensabaugh, Jr. et al.; U.S. Pat. No. 4,624,269 to Story et al.; U.S. Pat. No. 4,991,599 to Tibbetts; U.S. Pat. No. 4,987,907 to Townsend; U.S. Pat. No. 5,092,352 to Sprinkle, III et al.; U.S. Pat. No. 5,387,416 to White et al.; U.S. Pat. No. 6,668,839 to Williams; U.S. Pat. No. 6,834,654 to Williams; U.S. Pat. No. 6,953,040 to Atchley et al.; U.S. Pat. No. 7,032,601 to Atchley et al.; and U.S. Pat. No. 7,694,686 to Atchley et al.; US Pat. Pub. Nos. 2004/0020503 to Williams; 2005/0115580 to Quinter et al.; 2006/0191548 to Strickland et al.; 2007/0062549 to Holton, Jr. et al.; 2007/0186941 to Holton, Jr. et al.; 2007/0186942 to Strickland et al.; 2008/0029110 to Dube et al.; 2008/0029116 to Robinson et al.; 2008/0173317 to Robinson et al.; 2008/0209586 to Neilsen et al.; 2009/0065013 to Essen et al.; and 2010/0282267 to Atchley, as well as WO2004/095959 to Arnarp et al., each of which is incorporated herein by reference.

Smokeless tobacco product configurations that combine tobacco material, nicotine components, and/or other active ingredients, with various binders and fillers have been proposed more recently, with example product formats including lozenges, pastilles, gels, extruded forms, and the like. See, for example, the types of products described in US Patent App. Pub. Nos. 2008/0196730 to Engstrom et al.; 2008/0305216 to Crawford et al.; 2009/0293889 to Kumar et al.; 2010/0291245 to Gao et al; 2011/0139164 to Mua et al.; 2012/0037175 to Cantrell et al.; 2012/0055494 to Hunt et al.; 2012/0138073 to Cantrell et al.; 2012/0138074 to Cantrell et al.; 2013/0074855 to Holton, Jr.; 2013/0074856 to Holton, Jr.; 2013/0152953 to Mua et al.; 2013/0274296 to Jackson et al.; 2015/0068545 to Moldoveanu et al.; 2015/0101627 to Marshall et al.; and 2015/0230515 to Lampe et al., each of which is incorporated herein by reference.

BRIEF SUMMARY

Oral products are used by placing a nicotine containing matrix between the cheek and the gum. Nicotine is then released from the product and typically absorbed through the oral mucosa, thereby entering the blood stream where it is circulated systemically. Flavor stability and positive sensory attributes are important elements to a consumer-acceptable oral product. The organoleptic impact of flavors has been shown to be particularly sensitive to product pH. When the product pH exceeds ca. 7.0, the visual, aroma, and taste impact of some flavors degrades over time, and nicotine may evaporate from the product. This instability is particularly noticeable for certain flavors such as ethyl vanillin, lime, and cinnamon, which also cause darkening of an otherwise white product over time. However, lowering of pH increases the extent of nicotine present in the protonated form. As a dibasic alkaloid, nicotine is capable of accepting two protons (pyridine ring nitrogen: log $K_{a1}$=3.41; and pyrrolidine ring nitrogen: log $K_{a2}$=8.02), significantly changing the polarity. The overall polarity of nicotine increases from log(P)=1.09 (unprotonated nicotine) to −2.07 (for nicotine protonated on the pyrrolidine ring nitrogen). Passive diffusion of substances such as nicotine across membranes (e.g., mucosal membranes) is a function of molecule polarity and membrane properties, as well as molecular size and ionization (Kokate et al., *PharmSciTech* 2008, 9, 501-504).

Without wishing to be bound by theory, it is believed that downward shift in log P as a result of protonation state is the predominant driving force behind the reduction in nicotine absorption with descending pH. (Nair et al., *Journal of Pharmaceutical Sciences* 1997, 86, 257-262; Chen et al., *International Journal of Pharmaceutics* 1999, 184, 63-72; Adrian et al., *International Journal of Pharmaceutics* 2006, 311, 196-202). Specifically, as reported in Adrian et al., while there was still some diffusion across human buccal tissue in a perfusion cell for a nicotine solution at pH=6 (when nicotine is predominantly monoprotonated), the rate was greatly reduced relative a nicotine solution at pH 8.1 (by a factor of ~7).

The present disclosure generally provides a composition configured for oral use comprising a basic amine and an organic acid, an alkali metal salt of an organic acid, or a combination thereof, wherein the organic acid has a log P value from about 1 to about 12, such as from about 3 to about 10, or from about 3 to about 8. At least a portion of the basic amine is associated with at least a portion of the organic acid or the alkali metal salt thereof, the association in the form of a basic amine-organic acid salt, an ion pair between the basic amine and a conjugate base of the organic acid, or both. It has been found according to the present disclosure that certain carotenoid derivative having one or more carboxylic acids, and certain dicarboxylic acid monoesters, provide suitable ion pairing opportunities with a basic amine, for example, nicotine, and may further add desirable features to the composition comprising them, for example, color, a cooling sensation, reduced throat irritation, or combinations thereof.

Accordingly, in one aspect is provided a composition configured for oral use, the composition comprising: at least one filler; a basic amine; water; and an organic acid, an alkali metal salt of an organic acid, or a combination thereof, the organic acid having a log P value from about 1 to about 12, wherein at least a portion of the basic amine is associated with at least a portion of the organic acid or the alkali metal salt thereof, the association in the form of a basic amine-organic acid salt, an ion pair between the basic amine and a conjugate base of the organic acid, or both, and wherein the organic acid is a monoester of a dicarboxylic acid or a carotenoid derivative having one or more carboxylic acids.

In some embodiments, the organic acid has a log P value from about 3 to about 12. In some embodiments, the organic acid has a log P value from about 3 to about 10. In some embodiments, the organic acid has a log P value from about 3 to about 8.

In some embodiments, the organic acid is a menthyl or tocopherol monoester of a dicarboxylic acid. In some embodiments, the dicarboxylic acid is malonic acid, succinic acid, glutaric acid, adipic acid, fumaric acid, maleic acid, or a combination thereof. In some embodiments, the organic acid is tocopherol succinate, monomenthyl succinate, monomenthyl fumarate, monomenthyl glutarate, or a combination thereof.

In some embodiments, the organic acid is 2E,4E,6E,8E,10E,12E,14E,16Z,18E)-20-methoxy-4,8,13,17-tetramethyl-20-oxoicosa-2,4,6,8,10,12,14,16,18-nonaenoic acid (bixin) or an isomer thereof. In some embodiments, the organic acid is (2E,4E,6E,8E,10E,12E,14E,16E,18E)-4,8,13,17-tetramethylicosa-2,4,6,8,10,12,14,16,18-nonaenedioic acid (norbixin).

In some embodiments, the composition further comprises a solubility enhancer. In some embodiments, the solubility enhancer is glycerol or propylene glycol or another humectant as set forth herein.

In some embodiments, the composition comprises from about 0.05, about 0.1, about 1, about 1.5, about 2, or about 5, to about 10, about 15, or about 20 molar equivalents of the organic acid, the alkali metal salt thereof, or the combination thereof, relative to the basic amine, calculated as the amine free base. In some embodiments, the composition comprises from about 2 to about 10 molar equivalents of the organic acid, the alkali metal salt thereof, or the combination thereof, relative to the basic amine, calculated as the amine free base.

In some embodiments, the organic acid further comprises benzoic acid, an alkali metal salt thereof, or a combination thereof.

In some embodiments, the alkali metal is sodium or potassium.

In some embodiments, the composition comprises the organic acid and a sodium salt of the organic acid. In some embodiments, a ratio of the organic acid to the sodium salt of the organic acid is from about 0.1 to about 10.

In some embodiments, the pH of the composition is from about 4.0 to about 9.0. In some embodiments, the pH of the composition is from about 4.5 to about 7. In some embodiments, the pH of the composition is from about 5.5 to about 7. In some embodiments, wherein the pH of the composition is from about 4.0 to about 5.5. In some embodiments, the pH of the composition is from about 7.0 to about 9.0.

In some embodiments, the basic amine is nicotine. In some embodiments, the nicotine is present in an amount of from about 0.001 to about 10% by weight of the composition, calculated as the free base and based on the total weight of the composition.

In some embodiments, the at least one filler comprises a cellulose material. In some embodiments, the cellulose material comprises microcrystalline cellulose. In some embodiments, the at least one filler further comprises a cellulose derivative in an amount by weight of from about 1% to about 3%, based on the total weight of the composition. In some embodiments, the cellulose derivative is hydroxypropylcellulose.

In some embodiments, the composition comprises: from about 10 to about 50% of the at least one filler; and from about 5 to about 60% by weight of water, based on the total weight of the composition.

In some embodiments, the composition further comprises one or more active ingredients, one or more flavoring agents, one or more salts, one or more sweeteners, one or more binding agents, one or more humectants, one or more gums, a tobacco material, or combinations thereof.

In some embodiments, the composition further comprises one or more active ingredients selected from the group consisting of nutraceuticals, botanicals, stimulants, amino acids, vitamins, and cannabinoids.

In some embodiments, the composition comprises no more than about 10% by weight of a tobacco material, excluding any nicotine component present, based on the total weight of the composition. In some embodiments, the composition is free of tobacco material.

In some embodiments, the composition is enclosed in a pouch to form a pouched product, the composition optionally being in a granular form.

In some embodiments, the composition is in the form of a gel, pastille, gum, chew, melt, tablet, lozenge, granular material, or powder.

The disclosure includes, without limitations, the following embodiments.

Embodiment 1: A composition configured for oral use, the composition comprising: at least one filler; a basic amine; water; and an organic acid, an alkali metal salt of an organic acid, or a combination thereof, the organic acid having a log P value from about 1 to about 12, wherein at least a portion of the basic amine is associated with at least a portion of the organic acid or the alkali metal salt thereof, the association in the form of a basic amine-organic acid salt, an ion pair between the basic amine and a conjugate base of the organic acid, or both, and wherein the organic acid is a monoester of a dicarboxylic acid or is a carotenoid derivative having one or more carboxylic acids.

Embodiment 2: The composition of embodiment 1, wherein the organic acid has a log P value from about 3 to about 10, or from about 3 to about 8.

Embodiment 3: The composition of embodiment 1 or 2, wherein the organic acid is a menthyl or tocopherol monoester of a dicarboxylic acid.

Embodiment 4: The composition of embodiment 3, wherein the dicarboxylic acid is malonic acid, succinic acid, glutaric acid, adipic acid, fumaric acid, maleic acid, or a combination thereof.

Embodiment 5: The composition of any one of embodiments 1-3, wherein the organic acid is norbixin, bixin, or an isomer thereof.

Embodiment 6: The composition of any one of embodiments 1-3, wherein the organic acid is tocopherol succinate, monomenthyl succinate, monomenthyl fumarate, monomenthyl glutarate, or a combination thereof.

Embodiment 7: The composition of any one of embodiments 1-6, wherein the composition further comprises a solubility enhancer.

Embodiment 8: The composition of embodiment 7, wherein the solubility enhancer is glycerol or propylene glycol.

Embodiment 9: The composition of any one of embodiments 1-8, comprising from about 0.05, about 0.1, about 1, about 1.5, about 2, or about 5, to about 10, about 15, or about 20 molar equivalents of the organic acid, the alkali metal salt thereof, or the combination thereof, relative to the basic amine, calculated as the amine free base.

Embodiment 10: The composition of any one of embodiments 1-9, comprising from about 2 to about 10 molar equivalents of the organic acid, the alkali metal salt thereof, or the combination thereof, relative to the basic amine, calculated as the amine free base.

Embodiment 11: The composition of any one of embodiments 1-11, wherein the organic acid further comprises benzoic acid, an alkali metal salt thereof, or a combination thereof.

Embodiment 12: The composition of any one of embodiments 1-11, wherein the alkali metal is sodium or potassium.

Embodiment 13: The composition of any one of embodiments 1-12, comprising the organic acid and a sodium salt of the organic acid.

Embodiment 14: The composition of any one of embodiments 1-13, wherein a ratio of the organic acid to the sodium salt of the organic acid is from about 0.1 to about 10.

Embodiment 15: The composition of any one of embodiments 1-14, wherein the pH of the composition is from about 4.0 to about 9.0.

Embodiment 16: The composition of any one of embodiments 1-15, wherein the pH of the composition is from about 4.5 to about 7.

Embodiment 17: The composition of any one of embodiments 1-16, wherein the pH of the composition is from about 5.5 to about 7.

Embodiment 18: The composition of any one of embodiments 1-15, wherein the pH of the composition is from about 4.0 to about 5.5.

Embodiment 19: The composition of any one of embodiments 1-14, wherein the pH of the composition is from about 7.0 to about 9.0.

Embodiment 20: The composition of any one of embodiments 1-19, wherein the basic amine is nicotine.

Embodiment 21: The composition of embodiment 20, wherein the nicotine is present in an amount of from about 0.001 to about 10% by weight of the composition, calculated as the free base and based on the total weight of the composition.

Embodiment 22: The composition of any one of embodiments 1-21, wherein the at least one filler comprises a cellulose material.

Embodiment 23: The composition of any one of embodiments 1-22, wherein the cellulose material comprises microcrystalline cellulose.

Embodiment 24: The composition of any one of embodiments 1-23, wherein the at least one filler further comprises a cellulose derivative in an amount by weight of from about 1% to about 3%, based on the total weight of the composition.

Embodiment 25: The composition of embodiment 24, wherein the cellulose derivative is hydroxypropylcellulose.

Embodiment 26: The composition of any one of embodiments 1-25, comprising: from about 10 to about 50% of the at least one filler; and from about 5 to about 60% by weight of water, based on the total weight of the composition.

Embodiment 27: The composition of any one of embodiments 1-26, further comprising one or more active ingredients, one or more flavoring agents, one or more salts, one or more sweeteners, one or more binding agents, one or more humectants, one or more gums, a tobacco material, or combinations thereof.

Embodiment 28: The composition of any one of embodiments 1-27, further comprising one or more active ingredients selected from the group consisting of nutraceuticals, botanicals, stimulants, amino acids, vitamins, and cannabinoids.

Embodiment 29: The composition of any one of embodiments 1-28, comprising no more than about 10% by weight of a tobacco material, excluding any nicotine component present, based on the total weight of the composition.

Embodiment 30: The composition of any one of embodiments 1-28, wherein the composition is free of tobacco material.

Embodiment 31: The composition of any one of embodiments 1-30, enclosed in a pouch to form a pouched product, the composition optionally being in a granular form.

Embodiment 32: The composition of any one of embodiments 1-30, in the form of a gel, pastille, gum, chew, melt, tablet, lozenge, granular material, or powder.

Embodiment 33: A composition configured for oral use, the composition comprising: at least one filler; a basic amine (e.g., nicotine); water; and an organic acid, wherein the organic acid is a monoester of a dicarboxylic acid or is a carotenoid derivative having one or more carboxylic acids, such as wherein the organic acid is a menthyl or tocopherol monoester of a dicarboxylic acid, with example dicarboxylic acids including malonic acid, succinic acid, glutaric acid, adipic acid, fumaric acid, maleic acid, or a combination thereof, or wherein the organic acid is norbixin, bixin, or an isomer thereof, or wherein the organic acid is tocopherol succinate, monomenthyl succinate, monomenthyl fumarate, monomenthyl glutarate, or a combination thereof.

These and other features, aspects, and advantages of the disclosure will be apparent from a reading of the following detailed description together with the accompanying drawings, which are briefly described below. The invention includes any combination of two, three, four, or more of the above-noted embodiments as well as combinations of any two, three, four, or more features or elements set forth in this disclosure, regardless of whether such features or elements are expressly combined in a specific embodiment description herein. This disclosure is intended to be read holistically such that any separable features or elements of the disclosed invention, in any of its various aspects and embodiments, should be viewed as intended to be combinable unless the context clearly dictates otherwise.

BRIEF DESCRIPTION OF THE DRAWING

Having thus described aspects of the disclosure in the foregoing general terms, reference will now be made to the accompanying drawing, which is not necessarily drawn to scale. The drawing is exemplary only and should not be construed as limiting the disclosure.

FIG. 1 is a perspective view of a pouched product embodiment according to an example embodiment of the present disclosure, including a pouch or fleece at least partially filled with a composition configured for oral use.

DETAILED DESCRIPTION

The present disclosure will now be described more fully hereinafter with reference to example embodiments thereof. These example embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements.

As used in this specification and the claims, the singular forms “a,” “an,” and “the” include plural referents unless the context clearly dictates otherwise.

Reference to “dry weight percent” or “dry weight basis” refers to weight on the basis of dry ingredients (i.e., all ingredients except water). Reference to “wet weight” refers to the weight of the mixture including water. Unless otherwise indicated, reference to “weight percent” of a mixture reflects the total wet weight of the mixture (i.e., including water).

For customer satisfaction, it is desirable to provide a basic amine-containing composition configured for oral use which retains the initial basic amine content during storage, and which delivers substantially the full amount of basic amine initially present in the composition. The present disclosure provides compositions which combine a basic amine and a non-polar or lipophilic organic acid salt in the form of a basic amine-organic acid salt, an ion pair between the basic amine and a conjugate base of the organic acid, or both.

In some embodiments, the basic amine is nicotine. In certain embodiments, the presence of a non-polar or lipophilic organic acid, when ion paired with nicotine, may provide enhanced membrane permeability of the nicotine relative to a composition configured for oral use which includes a polar organic acid. Selection of certain organic acids, such as carotenoid derivatives having one or more carboxylic acids, or certain monoesters of dicarboxylic acids, may provide further desirable sensory qualities to the compositions, such as color or a cooling sensation, respectively.

Composition

The composition as disclosed herein comprises at least one filler; a basic amine, such as nicotine or a nicotine component; water; and an organic acid, an alkali metal salt of an organic acid, or a combination thereof, wherein the organic acid has a log P value from about 3 to about 12. At least a portion of the basic amine is associated with at least a portion of the organic acid or the alkali metal salt thereof. The association is in the form of a basic amine-organic acid salt, an ion pair between the basic amine and a conjugate base of the organic acid, or both. The relative amounts of the various components within the composition may vary, and typically are selected so as to provide the desired sensory and performance characteristics to the composition. The example individual components of the composition are described further herein below.

Ion Pairing

As disclosed herein, at least a portion of the basic amine is associated with at least a portion of the organic acid or the alkali metal salt thereof. Depending on multiple variables (concentration, pH, nature of the organic acid, and the like), the basic amine present in the composition can exist in multiple forms, including ion paired, in solution (i.e., fully solvated), as the free base, as a cation, as a salt, or any combination thereof. In some embodiments, the association between the basic amine and at least a portion of the organic acid or the alkali metal salt thereof is in the form of an ion pair between the basic amine and a conjugate base of the organic acid.

Ion pairing describes the partial association of oppositely charged ions in relatively concentrated solutions to form distinct chemical species called ion pairs. The strength of the association (i.e., the ion pairing) depends on the electrostatic force of attraction between the positive and negative ions (i.e., a protonated basic amine such as nicotine, and the conjugate base of the organic acid). By “conjugate base” is meant the base resulting from deprotonation of the corresponding acid (e.g., benzoate is the conjugate base of benzoic acid). On average, a certain population of these ion pairs exists at any given time, although the formation and dissociation of ion pairs is continuous. In the composition as disclosed herein, and/or upon oral use of said composition (e.g., upon contact with saliva), the basic amine, for example nicotine, and the conjugate base of the organic acid exist at least partially in the form of an ion pair. Without wishing to be bound by theory, it is believed that such ion pairing may minimize chemical degradation of the basic amine and/or enhance the oral availability of the basic amine (e.g., nicotine). At alkaline pH values (e.g., such as from about 7.5 to about 9), certain basic amines, for example nicotine, are largely present in the free base form, which has relatively low water solubility, and low stability with respect to evaporation and oxidative decomposition, but high mucosal availability. Conversely, at acidic pH values (such as from about 6.5 to about 4), certain basic amines, for example nicotine, are largely present in a protonated form, which has relatively high water solubility, and higher stability with respect to evaporation and oxidative decomposition, but low mucosal availability. Surprisingly, according to the present disclosure, it has been found that the properties of stability, solubility, and availability of the nicotine in a composition configured for oral use can be mutually enhanced through ion pairing or salt formation of nicotine with appropriate organic acids and/or their conjugate bases. Specifically, nicotine-organic acid ion pairs of moderate lipophilicity result in favorable stability and absorption properties. Lipophilicity is conveniently measured in terms of log P, the partition coefficient of a molecule between a lipophilic phase and an aqueous phase, usually octanol and water, respectively. An octanol-water partitioning favoring distribution of a basic amine-organic acid ion pair into octanol is predictive of good absorption of the basic amine present in the composition through the oral mucosa.

One of skill in the art will recognize that the extent of ion pairing in the disclosed composition, both before and during use by the consumer, may vary based on, for example, pH, the nature of the organic acid, the concentration of basic amine, the concentration of the organic acid or conjugate base of the organic acid present in the composition, the moisture content of the composition, the ionic strength of the composition, and the like. One of skill in the art will also recognize that ion pairing is an equilibrium process influenced by the foregoing variables. Accordingly, quantification of the extent of ion pairing is difficult or impossible by calculation or direct observation. However, the presence of ion pairing may be demonstrated through surrogate measures, such as partitioning of the basic amine between octanol and water, or by performing membrane permeation studies of aqueous solutions of the basic amine plus organic acids and/or their conjugate bases.

Organic Acid

As used herein, the term “organic acid” refers to an organic (i.e., carbon-based) compound that is characterized by acidic properties. Typically, organic acids are relatively weak acids (i.e., they do not dissociate completely in the presence of water), such as carboxylic acids ($—CO_2H$) or sulfonic acids ($—SO_2OH$). As used herein, reference to organic acid means an organic acid that is intentionally added. In this regard, an organic acid may be intentionally added as a specific composition ingredient as opposed to merely being inherently present as a component of another composition ingredient (e.g., the small amount of organic acid which may inherently be present in a composition ingredient, such as a tobacco material).

Suitable organic acids will typically have a range of lipophilicities (i.e., a polarity giving an appropriate balance of water and organic solubility). Typically, lipophilicities of suitable organic acids, as indicated by log P, will vary between about 1 and about 12 (more soluble in octanol than in water). In some embodiments, the organic acid has a log P value from about 1 to about 12, e.g., from about 1.0. about 1.5, about 2.0, about 2.5, about 3.0, about 3.5, about 4.0, about 4.5, about 5.0, about 5.5, about 6.0, about 6.5, about 7.0, about 7.5, or about 8.0, to about 8.5, about 9.0, about 9.5, about 10.0, about 10.5, about 11.0, about 11.5, or about 12.0.

Without wishing to be bound by theory, it is believed that moderately lipophilic organic acids (e.g., log P of from about 1.4 to about 4.5) produce ion pairs with nicotine which are of a polarity providing good octanol-water partitioning of the ion pair, and hence partitioning of nicotine, into octanol versus water. As discussed above, such partitioning into octanol is predictive of favorable oral availability.

In specific embodiments, the organic acid has a log P value from about 3.0 to about 8.0, about 10.0, or even 12.0. In some embodiments, the presence of certain solvents or solubilizing agents (e.g., inclusion in the composition of glycerin or propylene glycol) may be beneficial in solubilizing organic acids and the corresponding salts or ion pairs thereof with the basic amine for highly lipophilic organic acids (e.g., higher than about 4.5).

In some embodiments, the organic acid is a carboxylic acid or a sulfonic acid. The carboxylic acid or sulfonic acid functional group may be attached to any alkyl, cycloalkyl, heterocycloalkyl, aryl, or heteroaryl group having, for example, from one to twenty carbon atoms ($C_1$-$C_{20}$). In some embodiments, the organic acid is an alkyl, cycloalkyl, heterocycloalkyl, aryl, or heteroaryl carboxylic or sulfonic acid.

As used herein, "alkyl" refers to any straight chain or branched chain hydrocarbon. The alkyl group may be saturated (i.e., having all $sp^3$ carbon atoms), or may be unsaturated (i.e., having at least one site of unsaturation). As used herein, the term "unsaturated" refers to the presence of a carbon-carbon, $sp^2$ double bond in one or more positions within the alkyl group. Unsaturated alkyl groups may be mono- or polyunsaturated. Representative straight chain alkyl groups include, but are not limited to, methyl, ethyl, n-propyl, n-butyl, n-pentyl, and n-hexyl. Branched chain alkyl groups include, but are not limited to, isopropyl, sec-butyl, isobutyl, tert-butyl, isopentyl, and 2-methylbutyl. Representative unsaturated alkyl groups include, but are not limited to, ethylene or vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like. An alkyl group can be unsubstituted or substituted.

"Cycloalkyl" as used herein refers to a carbocyclic group, which may be mono- or bicyclic. Cycloalkyl groups include rings having 3 to 7 carbon atoms as a monocycle or 7 to 12 carbon atoms as a bicycle. Examples of monocyclic cycloalkyl groups include cyclopropyl, cyclobutyl, cyclopentyl, cyclohexyl, cycloheptyl, and cyclooctyl. A cycloalkyl group can be unsubstituted or substituted, and may include one or more sites of unsaturation (e.g., cyclopentenyl or cyclohexenyl).

The term "aryl" as used herein refers to a carbocyclic aromatic group. Examples of aryl groups include, but are not limited to, phenyl and naphthyl. An aryl group can be unsubstituted or substituted.

"Heteroaryl" and "heterocycloalkyl" as used herein refer to an aromatic or non-aromatic ring system, respectively, in which one or more ring atoms is a heteroatom, e.g. nitrogen, oxygen, and sulfur. The heteroaryl or heterocycloalkyl group comprises up to 20 carbon atoms and from 1 to 3 heteroatoms selected from N, O, and S. A heteroaryl or heterocycloalkyl may be a monocycle having 3 to 7 ring members (for example, 2 to 6 carbon atoms and 1 to 3 heteroatoms selected from N, O, and S) or a bicycle having 7 to 10 ring members (for example, 4 to 9 carbon atoms and 1 to 3 heteroatoms selected from N, O, and S), for example: a bicyclo[4,5], [5,5], [5,6], or [6,6] system. Examples of heteroaryl groups include by way of example and not limitation, pyridyl, thiazolyl, tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-carbazolyl, carbazolyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, benzotriazolyl, benzisoxazolyl, and isatinoyl. Examples of heterocycloalkyls include by way of example and not limitation, dihydroypyridyl, tetrahydropyridyl (piperidyl), tetrahydrothiophenyl, piperidinyl, 4-piperidonyl, pyrrolidinyl, 2-pyrrolidonyl, tetrahydrofuranyl, tetrahydropyranyl, bis-tetrahydropyranyl, tetrahydroquinolinyl, tetrahydroisoquinolinyl, decahydroquinolinyl, octahydroisoquinolinyl, piperazinyl, quinuclidinyl, and morpholinyl. Heteroaryl and heterocycloalkyl groups can be unsubstituted or substituted.

"Substituted" as used herein and as applied to any of the above alkyl, aryl, cycloalkyl, heteroaryl, heterocyclyl, means that one or more hydrogen atoms are each independently replaced with a substituent. Typical substituents include, but are not limited to, —Cl, Br, F, alkyl, —OH, $—OCH_3$, $NH_2$, $—NHCH_3$, $—N(CH_3)_2$, —CN, $—NC(=O)CH_3$, —C(=O)—, $—C(=O)NH_2$, and $—C(=O)N(CH_3)_2$. Wherever a group is described as "optionally substituted," that group can be substituted with one or more of the above substituents, independently selected for each occasion. In some embodiments, the substituent may be one or more methyl groups or one or more hydroxyl groups.

In some embodiments, the organic acid is an alkyl carboxylic acid. Non-limiting examples of alkyl carboxylic acids include formic acid, acetic acid, propionic acid, butyric acid, valeric acid, caproic acid, heptanoic acid, octanoic acid, nonanoic acid, decanoic acid, undecanoic acid, dodecanoic acid, stearic acid, oleic acid, linoleic acid, linolenic acid, and the like.

In some embodiments, the organic acid is an alkyl sulfonic acid. Non-limiting examples of alkyl sulfonic acids include propanesulfonic acid, heptanesulfonic acid, and octanesulfonic acid.

In some embodiments, the alkyl carboxylic or sulfonic acid is substituted with one or more hydroxyl groups. Non-limiting examples include glycolic acid, 4-hydroxybutyric acid, and lactic acid.

In some embodiments, an organic acid may include more than one carboxylic acid group or more than one sulfonic acid group (e.g., two, three, or more carboxylic acid groups).

Non-limiting examples include oxalic acid, fumaric acid, maleic acid, and glutaric acid. In organic acids containing multiple carboxylic acids (e.g., from two to four carboxylic acid groups), one or more of the carboxylic acid groups may be esterified. Non-limiting examples include succinic acid monoethyl ester, monomethyl fumarate, monomethyl or dimethyl citrate, and the like.

In some embodiments, the organic acid may include more than one carboxylic acid group and one or more hydroxyl groups. Non-limiting examples of such acids include tartaric acid, citric acid, and the like.

In some embodiments, the organic acid is an aryl carboxylic acid or an aryl sulfonic acid. Non-limiting examples of aryl carboxylic and sulfonic acids include benzoic acid, toluic acids, salicylic acid, benzenesulfonic acid, and p-toluenesulfonic acid.

Further non-limiting examples of organic acids which may be useful in certain embodiments include 2-(4-isobutylphenyl)propanoic acid, 2,2-dichloroacetic acid, 2-hydroxyethanesulfonic acid, 2-oxoglutaric acid, 4-acetamidobenzoic acid, 4-aminosalicylic acid, adipic acid, ascorbic acid (L), aspartic acid (L), alpha-methylbutyric acid, camphoric acid (+), camphor-10-sulfonic acid (+), cinnamic acid, cyclamic acid, dodecylsulfuric acid, ethane-1,2-disulfonic acid, ethanesulfonic acid, furoic acid, galactaric acid, gentisic acid, glucoheptonic acid, gluconic acid, glucuronic acid, glutamic acid, glycerophosphoric acid, glycolic acid, hippuric acid, isobutyric acid, isovaleric acid, lactobionic acid, lauric acid, levulinic acid, malic acid, malonic acid, mandelic acid, methanesulfonic acid, naphthalene-1,5-disulfonic acid, naphthalene-2-sulfonic acid, oleic acid, palmitic acid, pamoic acid, phenylacetic acid, pyroglutamic acid, pyruvic acid, sebacic acid, stearic acid, and undecylenic acid.

Examples of suitable acids include, but are not limited to, the list of organic acids in Table 1.

TABLE 1

Non-limiting examples of suitable organic acids

| Acid Name | log(P)* |
|---|---|
| benzoic acid | 1.9 |
| phenylacetic | 1.4 |
| p-toluic acid | 2.3 |
| ethyl benzoic acid | 2.9 |
| isopropyl benzoic acid | 3.5 |
| 4-phenylbutyric | 2.4 |
| 2-(4-Isobutylphenyl)propanoic acid | 3.5 |
| 2-napthoxyacetic acid | 2.5 |
| napthylacetic acid | 2.7 |
| heptanoic acid | 2.5 |
| octanoic acid | 3.05 |
| nonanoic acid | 3.5 |
| decanoic acid | 4.09 |
| 9-deceneoic acid | 3.3 |
| 2-deceneoic acid | 3.8 |
| 10-undecenoic acid | 3.9 |
| dodecandioic acid | 3.2 |
| dodecanoic acid | 4.6 |
| myristic acid | 5.3 |
| palmitic acid | 6.4 |
| stearic acid | 7.6 |
| cyclohexanebutanoic acid | 3.4 |
| 1-heptanesulfonic acid | 2.0 |
| 1-octanesulfonic acid | 2.5 |
| 1-nonanesulfonic acid | 3.1 |
| monooctyl succinate | 2.8 |
| tocopherol succinate | 10.2 |
| monomenthyl succinate | 3 |
| monomenthyl glutarate | 3.4 |
| norbixin ((2E,4E,6E,8E,10E,12E,14E,16E,18E)-4,8,13,17-tetramethylicosa-2,4,6,8,10,12,14,16,18-nonaenedioic acid) | 7.2 |
| bixin ((2E,4E,6E,8E,10E,12E,14E,16Z,18E)-20-methoxy-4,8,13,17-tetramethyl-20-oxoicosa-2,4,6,8,10,12,14,16,18-nonaenoic acid) | 7.5 |

*Values obtained from PubChem or calculated

The selection of organic acid may further depend on additional properties in addition to consideration of the log P value. For example, an organic acid should be one recognized as safe for human consumption, and which has acceptable flavor, odor, volatility, stability, and the like. Determination of appropriate organic acids is within the purview of one of skill in the art.

In some embodiments, the organic acid is a mono ester of a dicarboxylic acid or a poly-carboxylic acid. In some embodiments, the dicarboxylic acid is malonic acid, succinic acid, glutaric acid, adipic acid, fumaric acid, maleic acid, or a combination thereof. In some embodiments, the dicarboxylic acid is succinic acid, glutaric acid, fumaric acid, maleic acid, or a combination thereof. In some embodiments, the dicarboxylic acid is succinic acid, glutaric acid, or a combination thereof.

In some embodiments, the alcohol forming the mono ester of the dicarboxylic acid is a lipophilic alcohol. Examples of suitable lipophilic alcohols include, but are not limited to, octanol, menthol, and tocopherol. In some embodiments, the organic acid is an octyl mono ester of a dicarboxylic acid, such as monooctyl succinate, monooctyl fumarate, or the like. In some embodiments, the organic acid is a monomenthyl ester of a dicarboxylic acid. Certain menthyl esters may be desirable in oral compositions as described herein by virtue of the cooling sensation they may provide upon use of the product comprising the composition. In some embodiments, the organic acid is monomenthyl succinate, monomenthyl fumarate, monomenthyl glutarate, or a combination thereof. In some embodiments, the organic acid is a monotocopheryl ester of a dicarboxylic acid. Certain tocopheryl esters may be desirable in oral compositions as described herein by virtue of the antioxidant effects they may provide. In some embodiments, the organic acid is tocopheryl succinate, tocopheryl fumarate, tocopheryl glutarate, or a combination thereof.

In some embodiments, the organic acid is a carotenoid derivative having one or more carboxylic acids. Carotenoids are tetraterpenes, meaning that they are produced from 8 isoprene molecules and contain 40 carbon atoms. Accordingly, they are usually lipophilic due to the presence of long unsaturated aliphatic chains, and are generally yellow, orange, or red in color. Certain carotenoid derivatives can be advantageous in oral compositions by virtue of providing both ion pairing and serving as a colorant in the composition. In some embodiments, the organic acid is 2E,4E,6E,8E,10E,12E,14E,16Z,18E)-20-methoxy-4,8,13,17-tetramethyl-20-oxoicosa-2,4,6,8,10,12,14,16,18-nonaenoic acid (bixin) or an isomer thereof. Bixin is an apocarotenoid found in annatto seeds from the achiote tree (*Bixa orellana*) and is the naturally occurring pigment providing the reddish orange color to annatto. Bixin is soluble in fats and alcohols but insoluble in water, and is chemically unstable when isolated, converting via isomerization into the double bond isomer, trans-bixin (β-bixin), having the structure:

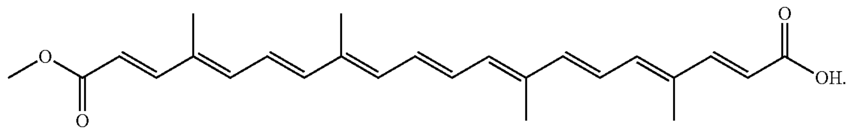 [SMILES: COC(=O)/C=C/C(C)=C/C=C/C(C)=C/C=C/C=C(C)/C=C/C=C(C)/C=C/C(=O)O]

In some embodiments, the organic acid is (2E,4E,6E,8E,10E,12E,14E,16E,18E)-4,8,13,17-tetramethylicosa-2,4,6,8,10,12,14,16,18-nonaenedioic acid (norbixin), a water-soluble hydrolysis product of bixin having the structure:

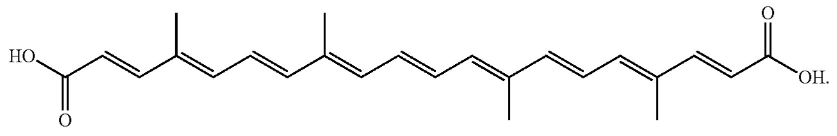 [SMILES: CC(/C=C/C=C(C)/C=C/C(=O)O)=C\C=C\C=C(C)\C=C\C=C(C)\C=C\C(=O)O]

In some embodiments, more than one organic acid may be present. For example, the composition may comprise two, or three, or four, or more organic acids. Accordingly, reference herein to "an organic acid" contemplates mixtures of two or more organic acids. The relative amounts of the multiple organic acids may vary. For example, a composition may comprise equal amounts of two, or three, or more organic acids, or may comprise different relative amounts. In this manner, it is possible to include certain organic acids (e.g., citric acid or myristic acid) which have a log P value outside the desired range, when combined with other organic acids to provide the desired average log P range for the combination. In some embodiments, it may be desirable to include organic acids in the composition which have log P values outside the desired range for purposes such as, but not limited to, providing desirable organoleptic properties, stability, as flavor components, and the like. Further, certain lipophilic organic acids have undesirable flavor and or aroma characteristics which would preclude their presence as the sole organic acid (e.g., in equimolar or greater quantities relative to nicotine). Without wishing to be bound by theory, it is believed that a combination of different organic acids may provide the desired ion pairing while the concentration of any single organic acid in the composition remains below the threshold which would be found objectionable from a sensory perspective.

In some embodiments, the composition comprises an organic acid which is a monoester of a dicarboxylic acid or is a carotenoid derivative having one or more carboxylic acids as described herein above, and further comprises an additional organic acid or salt thereof. In some embodiments, the additional organic acid is benzoic acid, an alkali metal salt thereof, or a combination thereof.

In some embodiments, the composition comprises an alkali metal salt of an organic acid. For example, at least a portion of the organic acid may be present in the composition in the form of an alkali metal salt. Suitable alkali metal salts include lithium, sodium, and potassium. In some embodiments, the alkali metal is sodium or potassium. In some embodiments, the alkali metal is sodium. In some embodiments, the composition comprises an organic acid and a sodium salt of the organic acid.

In some embodiments, the weight ratio of the organic acid to the sodium salt (or other alkali metal) of the organic acid is from about 0.1 to about 10, such as from about 0.1, about 0.25, about 0.3, about 0.5, about 0.75, or about 1, to about 2, about 5, or about 10. For example, in some embodiments, both an organic acid and the sodium salt thereof are added to the other components of the composition, wherein the organic acid is added in excess of the sodium salt, in equimolar quantities with the sodium salt, or as a fraction of the sodium salt. One of skill in the art will recognize that the relative amounts will be determined by the desired pH of the composition, as well as the desired ionic strength. For example, the organic acid may be added in a quantity to provide a desired pH level of the composition, while the alkali metal (e.g., sodium) salt is added in a quantity to provide the desired extent of ion pairing. As one of skill in the art will understand, the quantity of organic acid (i.e., the protonated form) present in the composition, relative to the alkali metal salt or conjugate base form present in the composition, will vary according to the pH of the composition and the pKa of the organic acid, as well as according to the actual relative quantities initially added to the composition.

The amount of organic acid or alkali metal salt thereof present in the composition, relative to the basic amine (e.g., nicotine), may vary. Generally, as the concentration of the organic acid (or the conjugate base thereof) increases, the percent of basic amine (e.g., nicotine) that is ion paired with the organic acid increases. This typically increases the partitioning of the basic amine (e.g., nicotine), in the form of an ion pair, into octanol versus water as measured by the log P (the $\log_{10}$ of the partitioning coefficient). In some embodiments, the composition comprises from about 0.05, about 0.1, about 1, about 1.5, about 2, or about 5, to about 10, about 15, or about 20 molar equivalents of the organic acid, the alkali metal salt thereof, or the combination thereof, relative to the basic amine (e.g., nicotine), calculated as the free base of the basic amine.

In some embodiments, the composition comprises from about 2 to about 10, or from about 2 to about 5 molar equivalents of the organic acid, the alkali metal salt thereof, or the combination thereof, relative to the basic amine (e.g., nicotine), on a free-base basis. In some embodiments, the organic acid, the alkali metal salt thereof, or the combination thereof, is present in a molar ratio with basic amine (e.g., nicotine) from about 2, about 3, about 4, or about 5, to about 6, about 7, about 8, about 9, or about 10. In embodiments wherein more than one organic acid, alkali metal salt thereof, or both, are present, it is to be understood that such molar ratios reflect the totality of the organic acids present.

In certain embodiments the organic acid inclusion is sufficient to provide a composition pH of from about 4.0 to about 9.0, such as from about 4.5 to about 7.0, or from about 5.5 to about 7.0, from about 4.0 to about 5.5, or from about 7.0 to about 9.0. In some embodiments, the organic acid inclusion is sufficient to provide a composition pH of from about 4.5 to about 6.5, for example, from about 4.5, about 5.0, or about 5.5, to about 6.0, or about 6.5. In some embodiments, the organic acid is provided in a quantity sufficient to provide a pH of the composition of from about 5.5 to about 6.5, for example, from about 5.5, about 5.6, about 5.7, about 5.8, about 5.9, or about 6.0, to about 6.1, about 6.2, about 6.3, about 6.4, or about 6.5. In other embodiments, a mineral acid (e.g., hydrochloric acid, sulfuric acid, phosphoric acid, or the like) is added to adjust the pH of the composition to the desired value.

In some embodiments, the organic acid is added as the free acid, either neat (i.e., native solid or liquid form) or as a solution in, e.g., water, to the other composition components. In some embodiments, the alkali metal salt of the organic acid is added, either neat or as a solution in, e.g., water, to the other composition components. In some embodiments, the organic acid and the basic amine (e.g., nicotine) are combined to form a salt, either before addition to the composition, or the salt is formed within and is present in the composition as such. In other embodiments, the organic acid and basic amine (e.g., nicotine) are present as individual components in the composition and form an ion pair upon contact with moisture (e.g., saliva in the mouth of the consumer).

In some embodiments, the organic acid is added as the free acid, either neat (i.e., native solid or liquid form) or as a solution in, e.g., water, to the other composition components. In some embodiments, the alkali metal salt of the organic acid is added, either neat or as a solution in, e.g., water, to the other composition components. In some embodiments, the organic acid and the basic amine (e.g., nicotine) are combined to form a salt, either before addition to the composition, or the salt is formed within and is present in the composition as such. In other embodiments, the organic acid and basic amine (e.g., nicotine) are present as individual components in the composition and form an ion pair upon contact with moisture (e.g., saliva in the mouth of the consumer).

In some embodiments, the oral composition comprises nicotine benzoate and sodium benzoate, wherein at least a portion of the nicotine and benzoate ions present are in an ion paired form. In some embodiments, the composition comprises nicotine benzoate, sodium benzoate, and an organic acid, an alkali metal salt of an organic acid, or a combination thereof, the organic acid having a log P value from about 1 to about 12, wherein the organic acid is a monoester of a dicarboxylic acid or is a carotenoid derivative having one or more carboxylic acids.

In some embodiments, the oral composition further comprises a solubility enhancer to increase the solubility of one or more of the organic acid or salt thereof. Suitable solubility enhancers include, but are not limited to, humectants as described herein, such as glycerol or propylene glycol.

Basic Amine

The composition as disclosed herein comprises a basic amine. By "basic amine" is meant a molecule including at least one basic amine functional group. Examples of basic amines include, but are not limited to, alkaloids. By "basic amine functional group" is meant a group containing a nitrogen atom having a lone pair of electrons. The basic amine functional group is attached to or incorporated within the molecule through one or more covalent bonds to the said nitrogen atom. The basic amine may be a primary, secondary, or tertiary amine, meaning the nitrogen bears one, two, or three covalent bonds to carbon atoms. By virtue of the lone pair of electrons on the nitrogen atom, such amines are termed "basic", meaning the lone electron pair is available for hydrogen bonding. The basicity (i.e., the electron density on the nitrogen atom and consequently the availability and strength of hydrogen bonding to the nitrogen atom) of the basic amine may be influenced by the nature of neighboring atoms, the steric bulk of the molecule, and the like.

Generally, the basic amine is released from the composition and absorbed through the oral mucosa, thereby entering the blood stream, where it is circulated systemically. Generally, the basic amine is present in or as an active ingredient in the composition, as described herein below. In some embodiments, the basic amine is nicotine or a nicotine component. By "nicotine component" is meant any suitable form of nicotine (e.g., free base, salt, or ion pair) for providing oral absorption of at least a portion of the nicotine present. Nicotine is released from the composition and absorbed through the oral mucosa, thereby entering the blood stream, where it is circulated systemically.

When present as the basic amine, the source of the nicotine may vary, and may be natural or synthetic. Nicotine may be tobacco-derived (e.g., a tobacco extract) or non-tobacco derived (e.g., synthetic or otherwise obtained). Most preferably, the nicotine is naturally occurring and obtained as an extract from a *Nicotiana* species (e.g., tobacco). The nicotine can have the enantiomeric form S(−)-nicotine, R(+)-nicotine, or a mixture of S(−)-nicotine and R(+)-nicotine. Most preferably, the nicotine is in the form of S(−)-nicotine (e.g., in a form that is virtually all S(−)-nicotine) or a racemic mixture composed primarily or predominantly of S(−)-nicotine (e.g., a mixture composed of about 95 weight parts S(−)-nicotine and about 5 weight parts R(+)-nicotine). Most preferably, the nicotine is employed in virtually pure form or in an essentially pure form. Highly preferred nicotine that is employed has a purity of greater than about 95 percent, more preferably greater than about 98 percent, and most preferably greater than about 99 percent, on a weight basis.

Typically, the nicotine component is selected from the group consisting of nicotine free base, nicotine as an ion pair, and a nicotine salt. In some embodiments, at least a portion of the nicotine is in its free base form. In some embodiments, at least a portion of the nicotine is present as a nicotine salt, or at least a portion of the nicotine is present as an ion pair with at least a portion of the organic acid or the conjugate base thereof, as disclosed herein above.

Typically, the nicotine component (calculated as the free base) is present in a concentration of at least about 0.001% by weight of the composition, such as in a range from about 0.001% to about 10%. In some embodiments, the nicotine component is present in a concentration from about 0.1% w/w to about 10% by weight, such as, e.g., from about from about 0.1% w/w, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, or about 10% by weight, calculated as the free base and based on the total weight of the composition. In some embodiments, the nicotine component is present in a concentration from about 0.1% w/w to about 3% by weight, such as, e.g., from about from about 0.1% w/w to about 2.5%, from about 0.1% to about 2.0%, from about 0.1% to about 1.5%, or from about 0.1% to about 1% by weight, calculated as the free base and based on the total weight of the composition.

As described herein above, the basic amine present in the composition may be nicotine or a nicotine component, or may be an active ingredient or a component of an active ingredient comprising a basic amine functionality. One of skill in the art will recognize that many active ingredients as described herein below are comprised of molecules which may be categorized as basic amines. Accordingly, the ion pairing of such basic amine-containing active ingredients with the lipophilic organic acids as described herein is contemplated. In such embodiments, the ion pair of the active ingredient and organic acid, alkali metal salt of the organic acid, or combination thereof may enhance the stability of the composition comprising the ion pair or enhance oral mucosal absorption of the active ingredient by virtue of the presence of the ion paired form of the active ingredient.

Filler

The composition as described herein comprises at least one filler. Fillers may fulfill multiple functions, such as enhancing certain organoleptic properties such as texture and mouthfeel, enhancing cohesiveness or compressibility of the product, and the like.

Generally, fillers are porous particulate materials and are cellulose-based. For example, suitable fillers are any non-tobacco plant material or derivative thereof, including cellulose materials derived from such sources. Examples of cellulosic non-tobacco plant material include cereal grains (e.g., maize, oat, barley, rye, buckwheat, and the like), sugar beet (e.g., FIBREX® brand filler available from International Fiber Corporation), bran fiber, and mixtures thereof. Non-limiting examples of derivatives of non-tobacco plant material include starches (e.g., from potato, wheat, rice, corn), natural cellulose, and modified cellulosic materials.

"Starch" as used herein may refer to pure starch from any source, modified starch, or starch derivatives. Starch is present, typically in granular form, in almost all green plants and in various types of plant tissues and organs (e.g., seeds, leaves, rhizomes, roots, tubers, shoots, fruits, grains, and stems). Starch can vary in composition, as well as in granular shape and size. Often, starch from different sources has different chemical and physical characteristics. A specific starch can be selected for inclusion in the mixture based on the ability of the starch material to impart a specific organoleptic property to composition. Starches derived from various sources can be used. For example, major sources of starch include cereal grains (e.g., rice, wheat, and maize) and root vegetables (e.g., potatoes and cassava). Other examples of sources of starch include acorns, arrowroot, arracacha, bananas, barley, beans (e.g., favas, lentils, mung beans, peas, chickpeas), breadfruit, buckwheat, *canna*, chestnuts, colacasia, katakuri, kudzu, malanga, millet, oats, oca, Polynesian arrowroot, sago, *sorghum*, sweet potato, *quinoa*, rye, tapioca, taro, tobacco, water chestnuts, and yams. Certain starches are modified starches. A modified starch has undergone one or more structural modifications, often designed to alter its high heat properties. Some starches have been developed by genetic modifications and are considered to be "modified" starches. Other starches are obtained and subsequently modified. For example, modified starches can be starches that have been subjected to chemical reactions, such as esterification, etherification, oxidation, depolymerization (thinning) by acid catalysis or oxidation in the presence of base, bleaching, transglycosylation and depolymerization (e.g., dextrinization in the presence of a catalyst), cross-linking, enzyme treatment, acetylation, hydroxypropylation, and/or partial hydrolysis. Other starches are modified by heat treatments, such as pregelatinization, dextrinization, and/or cold-water swelling processes. Certain modified starches include monostarch phosphate, distarch glycerol, distarch phosphate esterified with sodium trimetaphosphate, phosphate distarch phosphate, acetylated distarch phosphate, starch acetate esterified with acetic anhydride, starch acetate esterified with vinyl acetate, acetylated distarch adipate, acetylated distarch glycerol, hydroxypropyl starch, hydroxypropyl distarch glycerol, starch sodium octenyl succinate.

Additional examples of potential fillers include maltodextrin, dextrose, calcium carbonate, calcium phosphate, lactose, and sugar alcohols. Combinations of fillers can also be used. In some embodiments, the filler comprises or is a mixture of glucose and starch-derived polysaccharides. One such suitable mixture of glucose and starch-derived polysaccharides is EMDEX®, available from JRS PHARMA LP, USA, 2981 Route 22, Patterson, NY 12563-2359.

In some embodiments, the particulate filler is a cellulose material or cellulose derivative. One particularly suitable particulate filler for use in the compositions described herein is microcrystalline cellulose ("mcc"). The mcc may be synthetic or semi-synthetic, or it may be obtained entirely from natural celluloses. The mcc may be selected from the group consisting of AVICEL® grades PH-100, PH-102, PH-103, PH-105, PH-112, PH-113, PH-200, PH-300, PH-302, VIVACEL® grades 101, 102, 12, 20 and EMOCEL® grades 50M and 90M, and the like, and mixtures thereof. In one embodiment, the composition comprises mcc as the particulate filler. The quantity of mcc present may vary according to the desired properties.

The amount of filler can vary but is typically up to about 75 percent of the composition by weight, based on the total weight of the composition. A typical range of filler (e.g., mcc) within the composition can be from about 10 to about 75 percent by total weight of the composition, for example, from about 10, about 15, about 20, about 25, or about 30, to about 35, about 40, about 45, or about 50 weight percent (e.g., about 20 to about 50 weight percent or about 25 to about 45 weight percent). In certain embodiments, the amount of filler is at least about 10 percent by weight, such as at least about 20 percent, or at least about 25 percent, or at least about 30 percent, or at least about 35 percent, or at least about 40 percent, based on the total weight of the composition.

In one embodiment, the filler further comprises a cellulose derivative or a combination of such derivatives. In some embodiments, the composition comprises from about 1 to about 10% of the cellulose derivative by weight, based on the total weight of the composition, with certain embodiments comprising about 1 to about 5% by weight of cellulose derivative. In certain embodiments, the cellulose derivative is a cellulose ether (including carboxyalkyl ethers), meaning a cellulose polymer with the hydrogen of one or more hydroxyl groups in the cellulose structure replaced with an alkyl, hydroxyalkyl, or aryl group. Non-limiting examples of such cellulose derivatives include methylcellulose, hydroxypropylcellulose ("HPC"), hydroxypropylmethylcellulose ("HPMC"), hydroxyethyl cellulose, and carboxymethylcellulose ("CMC"). In one embodiment, the cellulose derivative is one or more of methylcellulose, HPC, HPMC, hydroxyethyl cellulose, and CMC. In one embodiment, the cellulose derivative is HPC. In some embodiments, the composition comprises from about 1 to about 3% HPC by weight, based on the total weight of the composition.

Water

The water content of the composition, prior to use by a consumer of the composition, may vary according to the desired properties. Typically, the composition is less than about 60 percent by weight of water, and generally is from about 1 to about 60% by weight of water, for example, from about 5 to about 55, about 10 to about 50, about 20 to about 45, or about 25 to about 40 percent water by weight, including water amounts of at least about 5% by weight, at least about 10% by weight, at least about 15% by weight, and at least about 20% by weight. In some embodiments, the composition is less than about 10 percent by weight of water, such as about 9 weight percent or less, about 7 weight percent or less, about 5 weight percent or less, about 4 weight percent or less, about 3 weight percent or less, or about 2 weight percent or less. In some embodiments, the water content of the composition is in a range from about 0.1 weight percent to about 10 weight percent, based on the total weight of the composition.

Active Ingredient

The composition as disclosed herein, in certain embodiments, comprises an active ingredient. As used herein, an "active ingredient" refers to one or more substances belonging to any of the following categories: API (active pharmaceutical substances), food additives, natural medicaments, and naturally occurring substances that can have an effect on humans. Example active ingredients include any ingredient known to impact one or more biological functions within the body, such as ingredients that furnish pharmacological activity or other direct effect in the diagnosis, cure, mitigation, treatment, or prevention of disease, or which affect the structure or any function of the body of humans (e.g., provide a stimulating action on the central nervous system, have an energizing effect, an antipyretic or analgesic action, or an otherwise useful effect on the body). In some embodiments, the active ingredient may be of the type generally referred to as dietary supplements, nutraceuticals, "phytochemicals" or "functional foods". These types of additives are sometimes defined in the art as encompassing substances typically available from naturally-occurring sources (e.g., botanical materials) that provide one or more advantageous biological effects (e.g., health promotion, disease prevention, or other medicinal properties), but are not classified or regulated as drugs.

Non-limiting examples of active ingredients include those falling in the categories of botanical ingredients, stimulants, amino acids, and/or pharmaceutical, nutraceutical, and medicinal ingredients (e.g., vitamins, such as B6, B12, and C, and/or cannabinoids, such as tetrahydrocannabinol (THC) and cannabidiol (CBD)). Each of these categories is further described herein below. The particular choice of active ingredients will vary depending upon the desired flavor, texture, and desired characteristics of the particular product.

The particular percentages of active ingredients present will vary depending upon the desired characteristics of the particular product. Typically, an active ingredient or combination thereof is present in a total concentration of at least about 0.001% by weight of the composition, such as in a range from about 0.001% to about 20%. In some embodiments, the active ingredient or combination of active ingredients is present in a concentration from about 0.1% w/w to about 10% by weight, such as, e.g., from about from about 0.5% w/w to about 10%, from about 1% to about 10%, from about 1% to about 5% by weight, based on the total weight of the composition. In some embodiments, the active ingredient or combination of active ingredients is present in a concentration of from about 0.001%, about 0.01%, about 0.1%, or about 1%, up to about 20% by weight, such as, e.g., from about from about 0.001%, about 0.002%, about 0.003%, about 0.004%, about 0.005%, about 0.006%, about 0.007%, about 0.008%, about 0.009%, about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% by weight, based on the total weight of the composition. Further suitable ranges for specific active ingredients are provided herein below.

Botanical

In some embodiments, the active ingredient comprises a botanical ingredient. As used herein, the term "botanical ingredient" or "botanical" refers to any plant material or fungal-derived material, including plant material in its natural form and plant material derived from natural plant materials, such as extracts or isolates from plant materials or treated plant materials (e.g., plant materials subjected to heat treatment, fermentation, bleaching, or other treatment processes capable of altering the physical and/or chemical nature of the material). For the purposes of the present disclosure, a "botanical" includes, but is not limited to, "herbal materials," which refer to seed-producing plants that do not develop persistent woody tissue and are often valued for their medicinal or sensory characteristics (e.g., teas or tisanes). Reference to botanical material as "non-tobacco" is intended to exclude tobacco materials (i.e., does not include any *Nicotiana* species).

When present, a botanical is typically at a concentration of from about 0.01% w/w to about 10% by weight, such as, e.g., from about from about 0.01% w/w, about 0.05%, about 0.1%, or about 0.5%, to about 1%, about 2%, about 3%, about 4%, about 5%, about 6%, about 7%, about 8%, about 9%, or about 10%, about 11%, about 12%, about 13%, about 14%, or about 15% by weight, based on the total weight of the effervescent composition.

The botanical materials useful in the present disclosure may comprise, without limitation, any of the compounds and sources set forth herein, including mixtures thereof. Certain botanical materials of this type are sometimes referred to as dietary supplements, nutraceuticals, "phytochemicals" or "functional foods." Certain botanicals, as the plant material or an extract thereof, have found use in traditional herbal medicine, and are described further herein.

Non-limiting examples of non-tobacco botanical materials include without limitation acai berry (*Euterpe oleracea martius*), acerola (*Malpighia glabra*), alfalfa, allspice, *Angelica* root, anise (e.g., star anise), annatto seed, apple (*Malus domestica*), apricot oil, ashwagandha, Bacopa monniera, baobab, basil (*Ocimum basilicum*), bay, bee balm, beet root, bergamot, blackberry (*Morus nigra*), black cohosh, black pepper, black tea, blueberries, boldo (*Peumus boldus*), borage, bugleweed, cacao, calamus root, camu (*Myrcaria dubia*), *Cannabis*/hemp, caraway seed, cardamom, cassis, catnip, catuaba, cayenne pepper, *Centella asiatica*, chaga mushroom, Chai-hu, chamomile, cherry, chervil, chive, chlorophyll, chocolate, cilantro, cinnamon (*Cinnamomum cassia*), citron grass (*Cymbopogon citratus*), *Citrus*, clary sage, cloves, coconut (*Cocos nucifera*), coffee, comfrey leaf and root, *cordyceps*, coriander seed, cranberry, cumin, curcumin, damiana, dandelion, *Dorstenia arifolia, Dorstenia odorata, Echinacea*, elderberry, elderflower, endro (*Anethum graveolens*), evening primrose, *eucalyptus*, fennel, feverfew, flax, *Galphimia glauca*, garlic, ginger (*Zingiber officinale*), *gingko biloba, ginseng*, goji berries, goldenseal, grape seed, grapefruit, grapefruit rose (*Citrus paradisi*), graviola (*Annona muricata*), green tea, guarana, gutu kola, hawthorn, hazel, hemp, *Hibiscus* flower (*Hibiscus sabdariffa*), honeybush, hops, jiaogulan, jambu (*Spilanthes oleraceae*), jasmine (*Jasminum officinale*), juniper berry (*Juniperus communis*), *Kaempferia parviflora* (*Thai ginseng*), kava, laurel, lavender, lemon (*Citrus limon*), lemon balm, lemongrass, licorice, lilac, Lion's mane, lutein, maca (*Lepidium meyenii*), mace, marjoram, matcha, milk thistle, mints (menthe), mulberry, *Nardostachys chinensis*, nutmeg, olive, oolong tea, orange (*Citrus sinensis*), oregano, *papaya*, paprika, pennyroyal, peppermint (*Mentha piperita*), pimento, potato peel, primrose, quercetin, quince, red clover, resveratrol, *Rhizoma gastrodiae, Rhodiola*, rooibos (red or green), rosehip (*Rosa canina*), rosemary, saffron, sage, Saint John's Wort, sandalwood, *Salvia* (*Salvia officinalis*), savory, saw palmetto, *Sceletium tortuosum, Schisandra, Silybum marianum*, Skullcap, spearmint, Spikenard, *spirulina*, slippery elm bark, *sorghum* bran hi-tannin, *sorghum* grain hi-tannin, spearmint (*Mentha spicata*), *spirulina*, star anise, sumac bran, tarragon, thyme, tisanes, turmeric, *Turnera aphrodisiaca*, uva *ursi*, valerian, vanilla, *Viola odorata*, wild yam root, wintergreen, *Withania somnifera*, yacon root, yellow dock, yerba mate, and yerba santa.

Stimulants

In some embodiments, the active ingredient comprises one or more stimulants. As used herein, the term "stimulant" refers to a material that increases activity of the central nervous system and/or the body, for example, enhancing focus, cognition, vigor, mood, alertness, and the like. Non-limiting examples of stimulants include caffeine, theacrine, theobromine, and theophylline. Theacrine (1,3,7,9-tetramethyluric acid) is a purine alkaloid which is structurally related to caffeine, and possesses stimulant, analgesic, and anti-inflammatory effects. Present stimulants may be natural, naturally derived, or wholly synthetic. For example, certain botanical materials (guarana, tea, coffee, cocoa, and the like) may possess a stimulant effect by virtue of the presence of e.g., caffeine or related alkaloids, and accordingly are "natural" stimulants. By "naturally derived" is meant the stimulant (e.g., caffeine, theacrine) is in a purified form, outside its natural (e.g., botanical) matrix. For example, caffeine can be obtained by extraction and purification from botanical sources (e.g., tea). By "wholly synthetic", it is meant that the stimulant has been obtained by chemical synthesis. In some embodiments, the active ingredient comprises caffeine. In some embodiments, the active ingredient is caffeine. In some embodiments, the caffeine is present in an encapsulated form. On example of an encapsulated caffeine is Vitashure®, available from Balchem Corp., 52 Sunrise Park Road, New Hampton, NY, 10958.

When present, a stimulant or combination of stimulants (e.g., caffeine, theacrine, and combinations thereof) is typically at a concentration of from about 0.1% w/w to about 15% by weight, such as, e.g., from about from about 0.1% w/w, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, about 10%, about 11%, about 12%, about 13%, about 14%, or about 15% by weight, based on the total weight of the composition.

Amino Acids

In some embodiments, the active ingredient comprises an amino acid. As used herein, the term "amino acid" refers to an organic compound that contains amine (—$NH_2$) and carboxyl (—COOH) or sulfonic acid ($SO_3H$) functional groups, along with a side chain (R group), which is specific to each amino acid. Amino acids may be proteinogenic or non-proteinogenic. By "proteinogenic" is meant that the amino acid is one of the twenty naturally occurring amino acids found in proteins. The proteinogenic amino acids include alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. By "non-proteinogenic" is meant that either the amino acid is not found naturally in protein or is not directly produced by cellular machinery (e.g., is the product of post-translational modification). Non-limiting examples of non-proteinogenic amino acids include gamma-aminobutyric acid (GABA), taurine (2-aminoethanesulfonic acid), theanine (L-γ-glutamylethylamide), hydroxyproline, and beta-alanine.

When present, an amino acid or combination of amino acids (e.g., taurine, theanine, and combinations thereof) is typically at a concentration of from about 0.1% w/w to about 15% by weight, such as, e.g., from about from about 0.1% w/w, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, about 10%, about 11%, about 12%, about 13%, about 14%, or about 15% by weight, based on the total weight of the effervescent composition.

Vitamins and Minerals

In some embodiments, the active ingredient comprises a vitamin or combination of vitamins. As used herein, the term "vitamin" refers to an organic molecule (or related set of molecules) that is an essential micronutrient needed for the proper functioning of metabolism in a mammal. There are thirteen vitamins required by human metabolism, which are: vitamin A (as all-trans-retinol, all-trans-retinyl-esters, as well as all-trans-beta-carotene and other provitamin A carotenoids), vitamin B1 (thiamine), vitamin B2 (riboflavin), vitamin B3 (niacin), vitamin B5 (pantothenic acid), vitamin B6 (pyridoxine), vitamin B7 (biotin), vitamin B9 (folic acid or folate), vitamin B12 (cobalamins), vitamin C (ascorbic acid), vitamin D (calciferols), vitamin E (tocopherols and tocotrienols), and vitamin K (quinones). In some embodiments, the active ingredient comprises vitamin C. In some embodiments, the active ingredient is a combination of vitamin C, caffeine, and taurine. In some embodiments, the active ingredient comprises one or more of vitamin B6 and B12. In some embodiments, the active ingredient comprises theanine and one or more of vitamin B6 and B12.

When present, a vitamin or combination of vitamins (e.g., vitamin B6, vitamin B12, vitamin E, vitamin C, or a combination thereof) is typically at a concentration of from about 0.01% w/w to about 1% by weight, such as, e.g., from about 0.01%, about 0.02%, about 0.03%, about 0.04%, about 0.05%, about 0.06%, about 0.07%, about 0.08%, about 0.09%, or about 0.1% w/w, to about 0.2%, about 0.3%, about 0.4%, about 0.5% about 0.6%, about 0.7%, about 0.8%, about 0.9%, or about 1% by weight, based on the total weight of the composition.

In some embodiments, the active ingredient comprises vitamin A. In some embodiments, the vitamin A is encapsulated. In some embodiments, the vitamin is vitamin B6, vitamin B12, vitamin E, vitamin C, or a combination thereof.

In some embodiments, the active ingredient comprises a mineral. As used herein, the term "mineral" refers to an inorganic molecule (or related set of molecules) that is an essential micronutrient needed for the proper functioning of various systems in a mammal. Non-limiting examples of minerals include iron, zinc, copper, selenium, chromium, cobalt, manganese, calcium, phosphorus, sulfur, magnesium, and the like. In some embodiments, the active ingredient comprises iron. Suitable sources of iron include, but are not limited to, ferrous salts such as ferrous sulfate and ferrous gluconate. In some embodiments, the iron is encapsulated.

Cannabinoids

In some embodiments, the active ingredient comprises one or more cannabinoids. As used herein, the term "cannabinoid" refers to a class of diverse natural or synthetic chemical compounds that acts on cannabinoid receptors (i.e., CB1 and CB2) in cells that alter neurotransmitter release in the brain. Cannabinoids are cyclic molecules exhibiting particular properties such as the ability to easily cross the blood-brain barrier. Cannabinoids may be naturally occurring (Phytocannabinoids) from plants such as *Cannabis*, (endocannabinoids) from animals, or artificially manufactured (synthetic cannabinoids). *Cannabis* species express at least 85 different phytocannabinoids, and these may be divided into subclasses, including cannabigerols, cannabichromenes, cannabidiols, tetrahydrocannabinols, cannabinols and cannabinodiols, and other cannabinoids, such as cannabigerol (CBG), cannabichromene (CBC), cannabidiol (CBD), tetrahydrocannabinol (THC), cannabinol (CBN) and cannabinodiol (CBDL), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), cannabinerolic acid, cannabidiolic acid (CBDA), cannabinol propyl variant (CBNV), cannabitriol (CBO), tetrahydrocannabmolic acid (THCA), and tetrahydrocannabivarinic acid (THCV A).

In some embodiments, the cannabinoid is selected from the group consisting of cannabigerol (CBG), cannabichromene (CBC), cannabidiol (CBD), tetrahydrocannabinol (THC), cannabinol (CBN) and cannabinodiol (CBDL), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), cannabinerolic acid, cannabidiolic acid (CBDA), Cannabinol propyl variant (CBNV), cannabitriol (CBO), tetrahydrocannabinolic acid (THCA), tetrahydrocannabivarinic acid (THCV A), and mixtures thereof. In some embodiments, the cannabinoid comprises at least tetrahydrocannabinol (THC).

In some embodiments, the cannabinoid is tetrahydrocannabinol (THC). In some embodiments, the cannabinoid comprises at least cannabidiol (CBD). In some embodiments, the cannabinoid is cannabidiol (CBD). In some embodiments, the CBD is synthetic CBD.

In some embodiments, the cannabinoid (e.g., CBD) is added to the composition in the form of an isolate. An isolate is an extract from a plant, such as *Cannabis*, where the active material of interest (in this case the cannabinoid, such as CBD) is present in a high degree of purity, for example greater than 95%, greater than 96%, greater than 97%, greater than 98%, or around 99% purity.

In some embodiments, the cannabinoid is an isolate of CBD in a high degree of purity, and the amount of any other cannabinoid in the composition is no greater than about 1% by weight of the composition, such as no greater than about 0.5% by weight of the composition, such as no greater than about 0.1% by weight of the composition, such as no greater than about 0.01% by weight of the composition.

The choice of cannabinoid and the particular percentages thereof which may be present within the disclosed composition will vary depending upon the desired flavor, texture, and other characteristics of the composition.

In some embodiments, the cannabinoid (such as CBD) is present in the composition in a concentration of at least about 0.001% by weight of the composition, such as in a range from about 0.001% to about 2% by weight of the composition. In some embodiments, the cannabinoid (such as CBD) is present in the composition in a concentration of from about 0.1% to about 1.5% by weight, based on the total weight of the composition. In some embodiments, the cannabinoid (such as CBD) is present in a concentration from about 0.4% to about 1.5% by weight, based on the total weight of the oral composition.

Alternatively, or in addition to the cannabinoid, the active ingredient may include a cannabimimetic, which is a class of compounds derived from plants other than *Cannabis* that have biological effects on the endocannabinoid system similar to cannabinoids. Examples include yangonin, alpha-amyrin or beta-amyrin (also classified as terpenes), cyanidin, curcumin (tumeric), catechin, quercetin, salvinorin A, N-acylethanolamines, and N-alkylamide lipids. Such compounds can be used in the same amounts and ratios noted herein for cannabinoids.

Terpenes

Active ingredients suitable for use in the present disclosure can also be classified as terpenes, many of which are associated with biological effects, such as calming effects. Terpenes are understood to have the general formula of $(C_5H_8)_n$ and include monoterpenes, sesquiterpenes, and diterpenes. Terpenes can be acyclic, monocyclic or bicyclic in structure. Some terpenes provide an entourage effect when used in combination with cannabinoids or cannabimimetics. Examples include beta-caryophyllene, linalool, limonene, beta-citronellol, linalyl acetate, pinene (alpha or beta), geraniol, carvone, eucalyptol, menthone, iso-menthone, piperitone, myrcene, beta-bourbonene, and germacrene, which may be used singly or in combination.

In some embodiments, the terpene is a terpene derivable from a phytocannabinoid producing plant, such as a plant from the stain of the *Cannabis sativa* species, such as hemp. Suitable terpenes in this regard include so-called "C10" terpenes, which are those terpenes comprising 10 carbon atoms, and so-called "C15" terpenes, which are those terpenes comprising 15 carbon atoms. In some embodiments, the active ingredient comprises more than one terpene. For example, the active ingredient may comprise one, two, three, four, five, six, seven, eight, nine, ten or more terpenes as defined herein. In some embodiments, the terpene is selected from pinene (alpha and beta), geraniol, linalool, limonene, carvone, eucalyptol, menthone, iso-menthone, piperitone, myrcene, beta-bourbonene, germacrene and mixtures thereof.

Antioxidants

In some embodiments, the active ingredient comprises one or more antioxidants. As used herein, the term "antioxidant" refers to a substance which prevents or suppresses oxidation by terminating free radical reactions, and may delay or prevent some types of cellular damage. Antioxidants may be naturally occurring or synthetic. Naturally occurring antioxidants include those found in foods and botanical materials. Non-limiting examples of antioxidants include certain botanical materials, vitamins, polyphenols, and phenol derivatives.

Examples of botanical materials which are associated with antioxidant characteristics include without limitation acai berry, alfalfa, allspice, annatto seed, apricot oil, basil, bee balm, wild bergamot, black pepper, blueberries, borage seed oil, bugleweed, cacao, calamus root, catnip, catuaba, cayenne pepper, chaga mushroom, chervil, cinnamon, dark chocolate, potato peel, grape seed, *ginseng, gingko biloba*, Saint John's Wort, saw palmetto, green tea, black tea, black cohosh, cayenne, chamomile, cloves, cocoa powder, cranberry, dandelion, grapefruit, honeybush, *echinacea*, garlic, evening primrose, feverfew, ginger, goldenseal, hawthorn, *Hibiscus* flower, jiaogulan, kava, lavender, licorice, marjoram, milk thistle, mints (menthe), oolong tea, beet root, orange, oregano, *papaya*, pennyroyal, peppermint, red clover, rooibos (red or green), rosehip, rosemary, sage, clary sage, savory, spearmint, *spirulina*, slippery elm bark, *sorghum* bran hi-tannin, *sorghum* grain hi-tannin, sumac bran, comfrey leaf and root, goji berries, gutu kola, thyme, turmeric, uva *ursi*, valerian, wild yam root, wintergreen, yacon root, yellow dock, yerba mate, yerba santa, bacopa monniera, *Withania somnifera*, Lion's mane, and *Silybum marianum*. Such botanical materials may be provided in fresh or dry form, essential oils, or may be in the form of an extracts. The botanical materials (as well as their extracts) often include compounds from various classes known to provide antioxidant effects, such as minerals, vitamins, isoflavones, phytoesterols, allyl sulfides, dithiolthiones, isothiocyanates, indoles, lignans, flavonoids, polyphenols, and carotenoids. Examples of compounds found in botanical extracts or oils include ascorbic acid, peanut endocarb, resveratrol, sulforaphane, beta-carotene, lycopene, lutein, co-enzyme Q, carnitine, quercetin, kaempferol, and the like. See, e.g., Santhosh et al., Phytomedicine, 12(2005) 216-220, which is incorporated herein by reference.

Non-limiting examples of other suitable antioxidants include citric acid, Vitamin E or a derivative thereof, a tocopherol, epicatechol, epigallocatechol, epigallocatechol gallate, erythorbic acid, sodium erythorbate, 4-hexylresorcinol, theaflavin, theaflavin monogallate A or B, theaflavin digallate, phenolic acids, glycosides, quercitrin, isoquercitrin, hyperoside, polyphenols, catechols, resveratrols, oleuropein, butylated hydroxyanisole (BHA), butylated hydroxytoluene (BHT), tertiary butylhydroquinone (TBHQ), and combinations thereof.

When present, an antioxidant is typically at a concentration of from about 0.001% w/w to about 10% by weight, such as, e.g., from about from about 0.001%, about 0.005%, about 0.01% w/w, about 0.05%, about 0.1%, or about 0.5%, to about 1%, about 2%, about 3%, about 4%, about 5%, about 6%, about 7%, about 8%, about 9%, or about 10%, based on the total weight of the composition.

Pharmaceutical Ingredients

In some embodiments, the active ingredient comprises an active pharmaceutical ingredient (API). The API can be any known agent adapted for therapeutic, prophylactic, or diagnostic use. These can include, for example, synthetic organic compounds, proteins and peptides, polysaccharides and other sugars, lipids, phospholipids, inorganic compounds (e.g., magnesium, selenium, zinc, nitrate), neurotransmitters or precursors thereof (e.g., serotonin, 5-hydroxytryptophan, oxitriptan, acetylcholine, dopamine, melatonin), and nucleic acid sequences, having therapeutic, prophylactic, or diagnostic activity. Non-limiting examples of APIs include analgesics and antipyretics (e.g., acetylsalicylic acid, acetaminophen, 3-(4-isobutylphenyl)propanoic acid), phosphatidylserine, myoinositol, docosahexaenoic acid (DHA, Omega-3), arachidonic acid (AA, Omega-6), S-adenosylmethionine (SAM), beta-hydroxy-beta-methylbutyrate (HMB), citicoline (cytidine-5'-diphosphate-choline), and cotinine.

When present, the amount of API may vary. For example, when present, an API is typically at a concentration of from about 0.001% w/w to about 10% by weight, such as, e.g., from about from about 0.01%, about 0.02%, about 0.03%, about 0.04%, about 0.05%, about 0.06%, about 0.07%, about 0.08%, about 0.09%, about 0.1% w/w, about 0.2%, about 0.3%, about 0.4%, about 0.5% about 0.6%, about 0.7%, about 0.8%, about 0.9%, or about 1%, to about 2%, about 3%, about 4%, about 5%, about 6%, about 7%, about 8%, about 9%, or about 10% by weight, based on the total weight of the composition.

Encapsulation and Stabilization of Active Ingredients

In some embodiments, the active ingredient as described herein may be sensitive to degradation (e.g., oxidative, photolytic, thermal, evaporative) during processing or upon storage of the composition. In such embodiments, the active ingredient (such as caffeine, vitamin A, and iron (Fe)) may be encapsulated, or the composition otherwise modified with suitable components (such as fillers, binders, and the like), to provide enhanced stability to the active ingredient. For example, binders such as functional celluloses (e.g., cellulose ethers including, but not limited to, hydroxypropyl cellulose) or alginate-based materials (e.g., cross linked alginate) may be employed to enhance stability of such actives toward degradation, or to provide extended and/or separate delivery of active ingredients. Additionally, encapsulated actives may need to be paired with an excipient in the composition to increase their solubility and/or bioavailability. Non-limiting examples of suitable excipients include beta-carotene, lycopene, Vitamin D, Vitamin E, Co-enzyme Q10, Vitamin K, and curcumin.

In other embodiments, in order to provide a desired concentration of the active ingredient by weight, an initial quantity of the active ingredient may be increased to compensate for a gradual degradative loss. Accordingly, larger initial amounts than those disclosed herein are contemplated by the present disclosure.

Flavoring Agent

In some embodiments, the composition as described herein comprises a flavoring agent. As used herein, a "flavoring agent" or "flavorant" is any flavorful or aromatic substance capable of altering the sensory characteristics associated with the oral product. Examples of sensory characteristics that can be modified by the flavoring agent include taste, mouthfeel, moistness, coolness/heat, and/or fragrance/aroma. Flavoring agents may be natural or synthetic, and the character of the flavors imparted thereby may be described, without limitation, as fresh, sweet, herbal, confectionary, floral, fruity, or spicy.

Flavoring agents may be imitation, synthetic or natural ingredients or blends thereof. Flavoring agents may include naturally occurring flavor materials, botanicals, extracts of botanicals, synthetically obtained materials, or combinations thereof (e.g., tobacco, *Cannabis*, licorice (liquorice), *hydrangea*, eugenol, Japanese white bark *magnolia* leaf, chamomile, fenugreek, clove, maple, matcha, menthol, Japanese mint, aniseed (anise), cinnamon, turmeric, Indian spices, Asian spices, herb, wintergreen, cherry, berry, red berry, cranberry, peach, apple, orange, mango, clementine, lemon, lime, tropical fruit, *papaya*, rhubarb, grape, durian, dragon fruit, cucumber, blueberry, mulberry, *Citrus* fruits, Drambuie, bourbon, scotch, whiskey, gin, tequila, rum, spearmint, peppermint, lavender, aloe vera, cardamom, celery, cascarilla, nutmeg, sandalwood, bergamot, geranium, khat, naswar, *betel*, shisha, pine, honey essence, rose oil, vanilla, lemon oil, orange oil, orange blossom, cherry blossom, *cassia*, caraway, cognac, jasmine, ylang-ylang, sage, fennel, wasabi, piment, ginger, coriander, coffee, hemp, a mint oil from any species of the genus *Mentha, eucalyptus*, star anise, cocoa, lemongrass, rooibos, flax, *Ginkgo biloba*, hazel, *Hibiscus*, laurel, mate, orange skin, rose, tea such as green tea or black tea, thyme, juniper, elderflower, basil, bay leaves, cumin, oregano, paprika, rosemary, saffron, lemon peel, mint, beefsteak plant, *curcuma*, cilantro, myrtle, cassis, valerian, pimento, mace, damien, marjoram, olive, lemon balm, lemon basil, chive, *carvi, verbena*, tarragon, limonene, thymol, camphene), flavor enhancers, bitterness receptor site blockers, sensorial receptor site activators or stimulators, sugars and/or sugar substitutes (e.g., sucralose, acesulfame potassium, aspartame, saccharine, cyclamates, lactose, sucrose, glucose, fructose, sorbitol, or mannitol), and other additives such as charcoal, chlorophyll, minerals, botanicals, or breath freshening agents.

Flavorants may further include flavor enhancers, bitterness receptor site blockers, sensorial receptor site activators or stimulators, and trigeminal sensates, As used herein, "trigeminal sensate" refers to a flavoring agent which has an effect on the trigeminal nerve, producing sensations including heating, cooling, tingling, and the like. Non-limiting examples of trigeminal sensate flavoring agents include capsaicin, citric acid, menthol, Sichuan buttons, erythritol, and cubebol. A suitable heat effect agent may be, but is not limited to, vanillyl ethyl ether, and a suitable cooling agent may be, but is not limited to eucalyptol or N-ethyl-p-menthane-3-carboxamide (WS-3).

Flavoring agents may be in any suitable form, for example, liquid such as an oil, solid such as a powder, or gas. In some instances, the flavoring agent may be provided in a spray-dried form or a liquid form. In some embodiments, a liquid flavorant is disposed (i.e., adsorbed or absorbed in or on) a porous particulate carrier, for example microcrystalline cellulose, which is then combined with the other composition ingredients.

The amount of flavoring agent utilized in the composition can vary, but is typically up to about 10% by weight, and certain embodiments are characterized by a flavoring agent content of at least about 0.1% by weight, such as about 0.5 to about 10%, about 1 to about 5%, or about 2 to about 4% weight, based on the total weight of the composition.

Taste Modifiers

In order to improve the organoleptic properties of a composition as disclosed herein, the composition may include one or more taste modifying agents ("taste modifiers") which may serve to mask, alter, block, or improve e.g., the flavor of a composition as described herein. Non-limiting examples of such taste modifiers include analgesic or anesthetic herbs, spices, and flavors which produce a perceived cooling (e.g., menthol, *eucalyptus*, mint), warming (e.g., cinnamon), or painful (e.g., capsaicin) sensation. Certain taste modifiers fall into more than one overlapping category.

In some embodiments, the taste modifier modifies one or more of bitter, sweet, salty, or sour tastes. In some embodiments, the taste modifier targets pain receptors. In some embodiments, the composition comprises an active ingredient having a bitter taste, and a taste modifier which masks or blocks the perception of the bitter taste. In some embodiments, the taste modifier is a substance which targets pain receptors (e.g., vanilloid receptors) in the user's mouth to mask e.g., a bitter taste of another component (e.g., an active ingredient). Suitable taste modifiers include, but are not limited to, capsaicin, gamma-amino butyric acid (GABA), adenosine monophosphate (AMP), lactisole, or a combination thereof.

When present, a representative amount of taste modifier is about 0.01% by weight or more, about 0.1% by weight or more, or about 1.0% by weight or more, but will typically make up less than about 10% by weight of the total weight of the composition, (e.g., from about 0.01%, about 0.05%, about 0.1%, or about 0.5%, to about 1%, about 5%, or about 10% by weight of the total weight of the composition).

Salts

In some embodiments, the composition may further comprise a salt (e.g., alkali metal salts), typically employed in an amount sufficient to provide desired sensory attributes to the composition. Non-limiting examples of suitable salts include sodium chloride, potassium chloride, ammonium chloride, flour salt, and the like.

When present, a representative amount of salt is about 0.5 percent by weight or more, about 1.0 percent by weight or more, or at about 1.5 percent by weight or more, but will typically make up about 10 percent or less of the total weight of the composition, or about 7.5 percent or less or about 5 percent or less (e.g., about 0.5 to about 5 percent by weight).

Sweeteners

In order to improve the sensory properties of the composition according to the disclosure, one or more sweeteners may be added. The sweeteners can be any sweetener or combination of sweeteners, in natural or artificial form, or as a combination of natural and artificial sweeteners. Examples of natural sweeteners include fructose, sucrose, glucose, maltose, mannose, galactose, lactose, *stevia*, honey, and the like. Examples of artificial sweeteners include sucralose, isomaltulose, maltodextrin, saccharin, aspartame, acesulfame K, neotame, and the like. In some embodiments, the sweetener comprises one or more sugar alcohols. Sugar alcohols are polyols derived from monosaccharides or disaccharides that have a partially or fully hydrogenated form. Sugar alcohols have, for example, about 4 to about 20 carbon atoms and include erythritol, arabitol, ribitol, isomalt, maltitol, dulcitol, iditol, mannitol, xylitol, lactitol, sorbitol, and combinations thereof (e.g., hydrogenated starch hydrolysates). In some embodiments, the sweetener is sucralose, acesulfame K, or a combination thereof.

When present, a sweetener or combination of sweeteners may make up from about 0.01 to about 20% or more of the of the composition by weight, for example, from about 0.01 to about 0.1, from about 0.1 to about 1%, from about 1 to about 5%, from about 5 to about 10%, or from about 10 to about 20% by weight, based on the total weight of the composition. In some embodiments, a combination of sweeteners is present at a concentration of from about 0.01% to about 0.1% by weight of the composition, such as about 0.01, about 0.02, about 0.03, about 0.04, about 0.05, about 0.06, about 0.07, about 0.08, about 0.09, or about 0.1% by weight of the composition. In some embodiments, a combination of sweeteners is present at a concentration of from about 0.1% to about 0.5% by weight of the composition, such as about 0.1, about 0.2, about 0.3, about 0.4, or about 0.5% by weight of the composition. In some embodiments, a combination of sweeteners is present at a concentration of from about 1% to about 3% by weight of the composition.

Binding Agents

A binder (or combination of binders) may be employed in certain embodiments. Typical binders can be organic or inorganic, or a combination thereof. Representative binders include povidone, sodium alginate, starch-based binders, pectin, carrageenan, pullulan, zein, and the like, and combinations thereof. A binder may be employed in amounts sufficient to provide the desired physical attributes and physical integrity to the composition. The amount of binder utilized in the composition can vary, but is typically up to about 30 weight percent, and certain embodiments are characterized by a binder content of at least about 0.1% by weight, such as about 1 to about 30% by weight, or about 5 to about 10% by weight, based on the total weight of the composition.

Other suitable binders include a gum, for example, a natural gum. As used herein, a natural gum refers to polysaccharide materials of natural origin that have binding properties, and which are also useful as a thickening or gelling agents. Representative natural gums derived from plants, which are typically water soluble to some degree, include xanthan gum, guar gum, gum arabic, ghatti gum, gum tragacanth, karaya gum, locust bean gum, gellan gum, and combinations thereof. When present, natural gum binder materials are typically present in an amount of up to about 5% by weight, for example, from about 0.1, about 0.2, about 0.3, about 0.4, about 0.5, about 0.6, about 0.7, about 0.8, about 0.9, or about 1%, to about 2, about 3, about 4, or about 5% by weight, based on the total weight of the composition.

Humectants

In certain embodiments, one or more humectants may be employed in the composition. Examples of humectants include, but are not limited to, polyols such as glycerin, propylene glycol, and the like. Where included, the humectant is typically provided in an amount sufficient to provide desired moisture attributes to the composition. Further, in some instances, the humectant may impart desirable flow characteristics to the composition for depositing in a mold.

When present, a humectant will typically make up about 5% or less of the weight of the composition (e.g., from about 0.5 to about 5% by weight). When present, a representative amount of humectant is about 0.1% to about 1% by weight, or about 1% to about 5% by weight, based on the total weight of the composition.

Buffering Agents

In certain embodiments, the composition of the present disclosure can comprise pH adjusters or buffering agents. Examples of pH adjusters and buffering agents that can be used include, but are not limited to, metal hydroxides (e.g., alkali metal hydroxides such as sodium hydroxide and potassium hydroxide), and other alkali metal buffers such as metal carbonates (e.g., potassium carbonate or sodium carbonate), or metal bicarbonates such as sodium bicarbonate, and the like. Non-limiting examples of suitable buffers include alkali metals acetates, glycinates, phosphates, glycerophosphates, citrates, carbonates, hydrogen carbonates, borates, or mixtures thereof.

Where present, the buffering agent is typically present in an amount less than about 5 percent based on the weight of the composition, for example, from about 0.5% to about 5%, such as, e.g., from about 0.75% to about 4%, from about 0.75% to about 3%, or from about 1% to about 2% by weight, based on the total weight of the composition.

Colorants

A colorant may be employed in amounts sufficient to provide the desired physical attributes to the composition. Natural or synthetic colorants, such as natural or synthetic dyes, food-grade colorants and pharmaceutical-grade colorants may be used. Examples of colorants include various dyes and pigments, such as caramel coloring and titanium dioxide. Natural colorants such as curcumin, beet juice extract, *spirulina*; also a variety of synthetic pigments may also be used. The amount of colorant utilized in the composition can vary, but when present is typically up to about 3% by weight, such as from about 0.1%, about 0.5%, or about 1%, to about 3% by weight, based on the total weight of the composition.

Tobacco Material

In some embodiments, the composition may include a tobacco material. The tobacco material can vary in species, type, and form. Generally, the tobacco material is obtained from for a harvested plant of the *Nicotiana* species. Example *Nicotiana* species include *N. tabacum, N. rustica, N. alata, N. arentsii, N. excelsior, N. forgetiana, N. glauca, N. glutinosa, N. gossei, N. kawakamii, N. knightiana, N. langsdorffi, N. otophora, N. setchelli, N. sylvestris, N. tomentosa, N. tomentosiformis, N. undulata, N.* x *sanderae, N. africana, N. amplexicaulis, N. benavidesii, N. bonariensis, N. debneyi, N. longiflora, N. maritina, N. megalosiphon, N. occidentalis, N. paniculata, N. plumbaginifolia, N. raimondii, N. rosulata, N. simulans, N. stocktonii, N. suaveolens, N. umbratica, N. velutina, N. wigandioides, N. acaulis, N. acuminata, N. attenuata, N. benthamiana, N. cavicola, N. clevelandii, N. cordifolia, N. corymbosa, N. fragrans, N. goodspeedii, N. linearis, N. miersii, N. nudicaulis, N. obtusifolia, N. occidentalis* subsp. Hersperis, *N. pauciflora, N. petunioides, N. quadrivalvis, N. repanda, N. rotundifolia, N. solanifolia*, and *N. spegazzinii*. Various representative other types of plants from the *Nicotiana* species are set forth in Goodspeed, *The Genus Nicotiana*, (Chonica Botanica) (1954); U.S. Pat. No. 4,660,577 to Sensabaugh, Jr. et al.; U.S. Pat. No. 5,387,416 to White et al., U.S. Pat. No. 7,025,066 to Lawson et al.; U.S. Pat. No. 7,798,153 to Lawrence, Jr. and U.S. Pat. No. 8,186,360 to Marshall et al.; each of which is incorporated herein by reference. Descriptions of various types of tobaccos, growing practices and harvesting practices are set forth in *Tobacco Production, Chemistry and Technology*, Davis et al. (Eds.) (1999), which is incorporated herein by reference.

*Nicotiana* species from which suitable tobacco materials can be obtained can be derived using genetic-modification or crossbreeding techniques (e.g., tobacco plants can be genetically engineered or crossbred to increase or decrease production of components, characteristics or attributes). See, for example, the types of genetic modifications of plants set forth in U.S. Pat. No. 5,539,093 to Fitzmaurice et al.; U.S. Pat. No. 5,668,295 to Wahab et al.; U.S. Pat. No. 5,705,624 to Fitzmaurice et al.; U.S. Pat. No. 5,844,119 to Weigl; U.S. Pat. No. 6,730,832 to Dominguez et al.; U.S. Pat. No. 7,173,170 to Liu et al.; U.S. Pat. No. 7,208,659 to Colliver et al. and U.S. Pat. No. 7,230,160 to Benning et al.; US Patent Appl. Pub. No. 2006/0236434 to Conkling et al.; and PCT WO2008/103935 to Nielsen et al. See, also, the types of tobaccos that are set forth in U.S. Pat. No. 4,660,577 to Sensabaugh, Jr. et al.; U.S. Pat. No. 5,387,416 to White et al.; and U.S. Pat. No. 6,730,832 to Dominguez et al., each of which is incorporated herein by reference.

The *Nicotiana* species can, in some embodiments, be selected for the content of various compounds that are present therein. For example, plants can be selected on the basis that those plants produce relatively high quantities of one or more of the compounds desired to be isolated therefrom. In certain embodiments, plants of the *Nicotiana* species (e.g., *Galpao commun* tobacco) are specifically grown for their abundance of leaf surface compounds. Tobacco plants can be grown in greenhouses, growth chambers, or outdoors in fields, or grown hydroponically.

Various parts or portions of the plant of the *Nicotiana* species can be included within a composition as disclosed herein. For example, virtually all of the plant (e.g., the whole plant) can be harvested, and employed as such. Alternatively, various parts or pieces of the plant can be harvested or separated for further use after harvest. For example, the flower, leaves, stem, stalk, roots, seeds, and various combinations thereof, can be isolated for further use or treatment.

In some embodiments, the tobacco material comprises tobacco leaf (lamina). The composition disclosed herein can include processed tobacco parts or pieces, cured and aged tobacco in essentially natural lamina and/or stem form, a tobacco extract, extracted tobacco pulp (e.g., using water as a solvent), or a mixture of the foregoing (e.g., a mixture that combines extracted tobacco pulp with granulated cured and aged natural tobacco lamina).

In certain embodiments, the tobacco material comprises solid tobacco material selected from the group consisting of lamina and stems. The tobacco that is used for the mixture most preferably includes tobacco lamina, or a tobacco lamina and stem mixture (of which at least a portion is smoke-treated). Portions of the tobaccos within the mixture may have processed forms, such as processed tobacco stems (e.g., cut-rolled stems, cut-rolled-expanded stems or cut-puffed stems), or volume expanded tobacco (e.g., puffed tobacco, such as dry ice expanded tobacco (DIET)). See, for example, the tobacco expansion processes set forth in U.S. Pat. No. 4,340,073 to de la Burde et al.; U.S. Pat. No. 5,259,403 to Guy et al.; and U.S. Pat. No. 5,908,032 to Poindexter, et al.; and U.S. Pat. No. 7,556,047 to Poindexter, et al., all of which are incorporated by reference. In addition, the d mixture optionally may incorporate tobacco that has been fermented. See, also, the types of tobacco processing techniques set forth in PCT WO2005/063060 to Atchley et al., which is incorporated herein by reference.

The tobacco material is typically used in a form that can be described as particulate (i.e., shredded, ground, granulated, or powder form). The manner by which the tobacco material is provided in a finely divided or powder type of form may vary. Preferably, plant parts or pieces are comminuted, ground or pulverized into a particulate form using equipment and techniques for grinding, milling, or the like. Most preferably, the plant material is relatively dry in form during grinding or milling, using equipment such as hammer mills, cutter heads, air control mills, or the like. For example, tobacco parts or pieces may be ground or milled when the moisture content thereof is less than about 15 weight percent or less than about 5 weight percent. Most preferably, the tobacco material is employed in the form of parts or pieces that have an average particle size between 1.4 millimeters and 250 microns. In some instances, the tobacco particles may be sized to pass through a screen mesh to obtain the particle size range required. If desired, air classification equipment may be used to ensure that small sized tobacco particles of the desired sizes, or range of sizes, may be collected. If desired, differently sized pieces of granulated tobacco may be mixed together.

The manner by which the tobacco is provided in a finely divided or powder type of form may vary. Preferably, tobacco parts or pieces are comminuted, ground or pulverized into a powder type of form using equipment and techniques for grinding, milling, or the like. Most preferably, the tobacco is relatively dry in form during grinding or milling, using equipment such as hammer mills, cutter heads, air control mills, or the like. For example, tobacco parts or pieces may be ground or milled when the moisture content thereof is less than about 15 weight percent to less than about 5 weight percent. For example, the tobacco plant or portion thereof can be separated into individual parts or pieces (e.g., the leaves can be removed from the stems, and/or the stems and leaves can be removed from the stalk). The harvested plant or individual parts or pieces can be further subdivided into parts or pieces (e.g., the leaves can be shredded, cut, comminuted, pulverized, milled or ground into pieces or parts that can be characterized as filler-type pieces, granules, particulates or fine powders). The plant, or parts thereof, can be subjected to external forces or pressure (e.g., by being pressed or subjected to roll treatment). When carrying out such processing conditions, the plant or portion thereof can have a moisture content that approximates its natural moisture content (e.g., its moisture content immediately upon harvest), a moisture content achieved by adding moisture to the plant or portion thereof, or a moisture content that results from the drying of the plant or portion thereof. For example, powdered, pulverized, ground or milled pieces of plants or portions thereof can have moisture contents of less than about 25 weight percent, often less than about 20 weight percent, and frequently less than about 15 weight percent.

For the preparation of oral compositions, it is typical for a harvested plant of the *Nicotiana* species to be subjected to a curing process. The tobacco materials incorporated within the composition as disclosed herein are those that have been appropriately cured and/or aged. Descriptions of various types of curing processes for various types of tobaccos are set forth in *Tobacco Production, Chemistry and Technology*, Davis et al. (Eds.) (1999). Examples of techniques and conditions for curing flue-cured tobacco are set forth in Nestor et al., *Beitrage Tabakforsch. Int.,* 20, 467-475 (2003) and U.S. Pat. No. 6,895,974 to Peele, which are incorporated herein by reference. Representative techniques and conditions for air curing tobacco are set forth in U.S. Pat. No. 7,650,892 to Groves et al.; Roton et al., *Beitrage Tabakforsch. Int.,* 21, 305-320 (2005) and Staaf et al., *Beitrage Tabakforsch. Int.,* 21, 321-330 (2005), which are incorporated herein by reference. Certain types of tobaccos can be subjected to alternative types of curing processes, such as fire curing or sun curing.

In certain embodiments, tobacco materials that can be employed include flue-cured or Virginia (e.g., K326), burley, sun-cured (e.g., Indian Kurnool and Oriental tobaccos, including Katerini, Prelip, Komotini, Xanthi and Yambol tobaccos), Maryland, dark, dark-fired, dark air cured (e.g., Madole, Passanda, Cubano, Jatin and Bezuki tobaccos), light air cured (e.g., North Wisconsin and *Galpao* tobaccos), Indian air cured, Red Russian and *Rustica* tobaccos, as well as various other rare or specialty tobaccos and various blends of any of the foregoing tobaccos.

The tobacco material may also have a so-called "blended" form. For example, the tobacco material may include a mixture of parts or pieces of flue-cured, burley (e.g., Malawi burley tobacco) and Oriental tobaccos (e.g., as tobacco composed of, or derived from, tobacco lamina, or a mixture of tobacco lamina and tobacco stem). For example, a representative blend may incorporate about 30 to about 70 parts burley tobacco (e.g., lamina, or lamina and stem), and about 30 to about 70 parts flue cured tobacco (e.g., stem, lamina, or lamina and stem) on a dry weight basis. Other example tobacco blends incorporate about 75 parts flue-cured tobacco, about 15 parts burley tobacco, and about 10 parts Oriental tobacco; or about 65 parts flue-cured tobacco, about 25 parts burley tobacco, and about 10 parts Oriental tobacco; or about 65 parts flue-cured tobacco, about 10 parts burley tobacco, and about 25 parts Oriental tobacco; on a dry weight basis. Other example tobacco blends incorporate about 20 to about 30 parts Oriental tobacco and about 70 to about 80 parts flue-cured tobacco on a dry weight basis.

Tobacco materials used in the present disclosure can be subjected to, for example, fermentation, bleaching, and the like. If desired, the tobacco materials can be, for example, irradiated, pasteurized, or otherwise subjected to controlled heat treatment. Such treatment processes are detailed, for example, in U.S. Pat. No. 8,061,362 to Mua et al., which is incorporated herein by reference. In certain embodiments, tobacco materials can be treated with water and an additive capable of inhibiting reaction of asparagine to form acrylamide upon heating of the tobacco material (e.g., an additive selected from the group consisting of lysine, glycine, histidine, alanine, methionine, cysteine, glutamic acid, aspartic acid, proline, phenylalanine, valine, arginine, compositions incorporating di- and trivalent cations, asparaginase, certain non-reducing saccharides, certain reducing agents, phenolic compounds, certain compounds having at least one free thiol group or functionality, oxidizing agents, oxidation catalysts, natural plant extracts (e.g., rosemary extract), and combinations thereof. See, for example, the types of treatment processes described in U.S. Pat. Nos. 8,434,496, 8,944,072, and 8,991,403 to Chen et al., which are all incorporated herein by reference. In certain embodiments, this type of treatment is useful where the original tobacco material is subjected to heat in the processes previously described.

In some embodiments, the type of tobacco material is selected such that it is initially visually lighter in color than other tobacco materials to some degree (e.g., whitened or bleached). Tobacco pulp can be whitened in certain embodiments according to any means known in the art. For example, bleached tobacco material produced by various whitening methods using various bleaching or oxidizing agents and oxidation catalysts can be used. Example oxidizing agents include peroxides (e.g., hydrogen peroxide), chlorite salts, chlorate salts, perchlorate salts, hypochlorite salts, ozone, ammonia, potassium permanganate, and combinations thereof. Example oxidation catalysts are titanium dioxide, manganese dioxide, and combinations thereof. Processes for treating tobacco with bleaching agents are discussed, for example, in U.S. Pat. No. 787,611 to Daniels, Jr.; U.S. Pat. No. 1,086,306 to Oelenheinz; U.S. Pat. No. 1,437,095 to Delling; U.S. Pat. No. 1,757,477 to Rosenhoch; U.S. Pat. No. 2,122,421 to Hawkinson; U.S. Pat. No. 2,148,147 to Baier; U.S. Pat. No. 2,170,107 to Baier; U.S. Pat. No. 2,274,649 to Baier; U.S. Pat. No. 2,770,239 to Prats et al.; U.S. Pat. No. 3,612,065 to Rosen; U.S. Pat. No. 3,851,653 to Rosen; U.S. Pat. No. 3,889,689 to Rosen; U.S. Pat. No. 3,943,940 to Minami; U.S. Pat. No. 3,943,945 to Rosen; U.S. Pat. No. 4,143,666 to Rainer; U.S. Pat. No. 4,194,514 to Campbell; U.S. Pat. Nos. 4,366,823, 4,366,824, and 4,388,933 to Rainer et al.; U.S. Pat. No. 4,641,667 to Schmekel et al.; U.S. Pat. No. 5,713,376 to Berger; U.S. Pat. No. 9,339,058 to Byrd Jr. et al.; U.S. Pat. No. 9,420,825 to Beeson et al.; and U.S. Pat. No. 9,950,858 to Byrd Jr. et al.; as well as in US Pat. App. Pub. Nos. 2012/0067361 to Bjorkholm et al.; 2016/0073686 to Crooks; 2017/0020183 to Bjorkholm; and 2017/0112183 to Bjorkholm, and in PCT Publ. Appl. Nos. WO1996/031255 to Giolvas and WO2018/083114 to Bjorkholm, all of which are incorporated herein by reference.

In some embodiments, the whitened tobacco material can have an ISO brightness of at least about 50%, at least about 60%, at least about 65%, at least about 70%, at least about 75%, or at least about 80%. In some embodiments, the whitened tobacco material can have an ISO brightness in the range of about 50% to about 90%, about 55% to about 75%, or about 60% to about 70%. ISO brightness can be measured according to ISO 3688:1999 or ISO 2470-1:2016.

In some embodiments, the whitened tobacco material can be characterized as lightened in color (e.g., "whitened") in comparison to an untreated tobacco material. White colors are often defined with reference to the International Commission on Illumination's (CIE's) chromaticity diagram. The whitened tobacco material can, in certain embodiments, be characterized as closer on the chromaticity diagram to pure white than an untreated tobacco material.

In various embodiments, the tobacco material can be treated to extract a soluble component of the tobacco material therefrom. "Tobacco extract" as used herein refers to the isolated components of a tobacco material that are extracted from solid tobacco pulp by a solvent that is brought into contact with the tobacco material in an extraction process. Various extraction techniques of tobacco materials can be used to provide a tobacco extract and tobacco solid material. See, for example, the extraction processes described in US Pat. Appl. Pub. No. 2011/0247640 to Beeson et al., which is incorporated herein by reference. Other example techniques for extracting components of tobacco are described in U.S. Pat. No. 4,144,895 to Fiore; U.S. Pat. No. 4,150,677 to Osborne, Jr. et al.; U.S. Pat. No. 4,267,847 to Reid; U.S. Pat. No. 4,289,147 to Wildman et al.; U.S. Pat. No. 4,351,346 to Brummer et al.; U.S. Pat. No. 4,359,059 to Brummer et al.; U.S. Pat. No. 4,506,682 to Muller; U.S. Pat. No. 4,589,428 to Keritsis; U.S. Pat. No. 4,605,016 to Soga et al.; U.S. Pat. No. 4,716,911 to Poulose et al.; U.S. Pat. No. 4,727,889 to Niven, Jr. et al.; U.S. Pat. No. 4,887,618 to Bernasek et al.; U.S. Pat. No. 4,941,484 to Clapp et al.; U.S. Pat. No. 4,967,771 to Fagg et al.; U.S. Pat. No. 4,986,286 to Roberts et al.; U.S. Pat. No. 5,005,593 to Fagg et al.; U.S. Pat. No. 5,018,540 to Grubbs et al.; U.S. Pat. No. 5,060,669 to White et al.; U.S. Pat. No. 5,065,775 to Fagg; U.S. Pat. No. 5,074,319 to White et al.; U.S. Pat. No. 5,099,862 to White et al.; U.S. Pat. No. 5,121,757 to White et al.; U.S. Pat. No. 5,131,414 to Fagg; U.S. Pat. No. 5,131,415 to Munoz et al.; U.S. Pat. No. 5,148,819 to Fagg; U.S. Pat. No. 5,197,494 to Kramer; U.S. Pat. No. 5,230,354 to Smith et al.; U.S. Pat. No. 5,234,008 to Fagg; U.S. Pat. No. 5,243,999 to Smith; U.S. Pat. No. 5,301,694 to Raymond et al.; U.S. Pat. No. 5,318,050 to Gonzalez-Parra et al.; U.S. Pat. No. 5,343,879 to Teague; U.S. Pat. No. 5,360,022 to Newton; U.S. Pat. No. 5,435,325 to Clapp et al.; U.S. Pat. No. 5,445,169 to Brinkley et al.; U.S. Pat. No. 6,131,584 to Lauterbach; U.S. Pat. No. 6,298,859 to Kierulff et al.; U.S. Pat. No. 6,772,767 to Mua et al.; and U.S. Pat. No. 7,337,782 to Thompson, all of which are incorporated by reference herein.

Typical inclusion ranges for tobacco materials can vary depending on the nature and type of the tobacco material, and the intended effect on the final mixture, with an example range of up to about 30% by weight (or up to about 20% by weight or up to about 10% by weight or up to about 5% by weight), based on total weight of the composition (e.g., about 0.1 to about 15% by weight). In some embodiments, the compositions of the disclosure can be characterized as completely free or substantially free of tobacco material (other than purified nicotine as an active ingredient). For example, certain embodiments can be characterized as having less than 1% by weight, or less than 0.5% by weight, or less than 0.1% by weight of tobacco material, or 0% by weight of tobacco material.

Oral Care Additives

In some embodiments, the composition comprises an oral care ingredient (or mixture of such ingredients). Oral care ingredients provide the ability to inhibit tooth decay or loss, inhibit gum disease, relieve mouth pain, whiten teeth, or otherwise inhibit tooth staining, elicit salivary stimulation, inhibit breath malodor, freshen breath, or the like. For example, effective amounts of ingredients such as thyme oil, *eucalyptus* oil and zinc (e.g., such as the ingredients of formulations commercially available as ZYTEX® from Discus Dental) can be incorporated into the composition.

Other examples of ingredients that can be incorporated in desired effective amounts within the present composition can include those that are incorporated within the types of oral care compositions set forth in Takahashi et al., Oral Microbiology and Immunology, 19(1), 61-64 (2004); U.S. Pat. No. 6,083,527 to Thistle; and US Pat. Appl. Pub. Nos. 2006/0210488 to Jakubowski and 2006/02228308 to Cummins et al. Other exemplary ingredients of tobacco containing-formulation include those contained in formulations marketed as MALTISORB® by Roquette and DENTIZYME® by NatraRx. When present, a representative amount of oral care additive is at least about 1%, often at least about 3%, and frequently at least about 5% of the total dry weight of the effervescent composition. The amount of oral care additive within the effervescent composition will not typically exceed about 30%, often will not exceed about 25%, and frequently will not exceed about 20%, of the total dry weight of the effervescent composition.

Processing Aids

If necessary for downstream processing of the composition, such as granulation, mixing, or molding, a flow aid can also be added to the composition in order to enhance flowability of the composition. In some embodiments, the composition (e.g., melt and chew forms) may be surface treated with anti-stick agents, such as oils, silicones, and the like. Exemplary flow aids include microcrystalline cellulose, silica, polyethylene glycol, stearic acid, calcium stearate, magnesium stearate, zinc stearate, sodium stearyl fumarate, canauba wax, and combinations thereof. In some embodiments, the flow aid is sodium stearyl fumarate.

When present, a representative amount of flow aid may make up at least about 0.5 percent or at least about 1 percent, of the total dry weight of the composition. Preferably, the amount of flow aid within the composition will not exceed about 5 percent, and frequently will not exceed about 3 percent, of the total dry weight of the composition.

Other Additives

Other additives can be included in the disclosed composition. For example, the composition can be processed, blended, formulated, combined and/or mixed with other materials or ingredients. The additives can be artificial or can be obtained or derived from herbal or biological sources. Examples of further types of additives include thickening or gelling agents (e.g., fish gelatin), emulsifiers, preservatives (e.g., potassium sorbate and the like), disintegration aids, or combinations thereof. See, for example, those representative components, combination of components, relative amounts of those components, and manners and methods for employing those components, set forth in U.S. Pat. No. 9,237,769 to Mua et al., U.S. Pat. No. 7,861,728 to Holton, Jr. et al., US Pat. App. Pub. No. 2010/0291245 to Gao et al., and US Pat. App. Pub. No. 2007/0062549 to Holton, Jr. et al., each of which is incorporated herein by reference.

Typical inclusion ranges for such additional additives can vary depending on the nature and function of the additive and the intended effect on the final composition, with an example range of up to about 10% by weight, based on total weight of the composition (e.g., about 0.1 to about 5% by weight).

The aforementioned additives can be employed together (e.g., as additive formulations) or separately (e.g., individual additive components can be added at different stages involved in the preparation of the final mixture). Furthermore, the aforementioned types of additives may be encapsulated as provided in the final product or composition. Example encapsulated additives are described, for example, in WO2010/132444 to Atchley, which has been previously incorporated by reference herein.

Particulate

In some embodiments, any one or more of the filler, tobacco material, other composition components, and the overall composition described herein can be described as a particulate material. As used herein, the term "particulate" refers to a material in the form of a plurality of individual particles, some of which can be in the form of an agglomerate of multiple particles, wherein the particles have an average length to width ratio less than 2:1, such as less than 1.5:1, such as about 1:1. In various embodiments, the particles of a particulate material can be described as substantially spherical or granular.

The particle size of a particulate material may be measured by sieve analysis. As the skilled person will readily appreciate, sieve analysis (otherwise known as a gradation test) is a method used to measure the particle size distribution of a particulate material. Typically, sieve analysis involves a nested column of sieves which comprise screens, preferably in the form of wire mesh cloths. A pre-weighed sample may be introduced into the top or uppermost sieve in the column, which has the largest screen openings or mesh size (i.e. the largest pore diameter of the sieve). Each lower sieve in the column has progressively smaller screen openings or mesh sizes than the sieve above. Typically, at the base of the column of sieves is a receiver portion to collect any particles having a particle size smaller than the screen opening size or mesh size of the bottom or lowermost sieve in the column (which has the smallest screen opening or mesh size).

In some embodiments, the column of sieves may be placed on or in a mechanical agitator. The agitator causes the vibration of each of the sieves in the column. The mechanical agitator may be activated for a pre-determined period of time in order to ensure that all particles are collected in the correct sieve. In some embodiments, the column of sieves is agitated for a period of time from 0.5 minutes to 10 minutes, such as from 1 minute to 10 minutes, such as from 1 minute to 5 minutes, such as for approximately 3 minutes. Once the agitation of the sieves in the column is complete, the material collected on each sieve is weighed. The weight of each sample on each sieve may then be divided by the total weight in order to obtain a percentage of the mass retained on each sieve. As the skilled person will readily appreciate, the screen opening sizes or mesh sizes for each sieve in the column used for sieve analysis may be selected based on the granularity or known maximum/minimum particle sizes of the sample to be analysed. In some embodiments, a column of sieves may be used for sieve analysis, wherein the column comprises from 2 to 20 sieves, such as from 5 to 15 sieves. In some embodiments, a column of sieves may be used for sieve analysis, wherein the column comprises 10 sieves. In some embodiments, the largest screen opening or mesh sizes of the sieves used for sieve analysis may be 1000 μm, such as 500 μm, such as 400 μm, such as 300 μm.

In some embodiments, any particulate material referenced herein (e.g., filler, tobacco material, and the overall composition) can be characterized as having at least 50% by weight of particles with a particle size as measured by sieve analysis of no greater than about 1000 μm, such as no greater than about 500 μm, such as no greater than about 400 μm, such as no greater than about 350 μm, such as no greater than about 300 μm. In some embodiments, at least 60% by weight of the particles of any particulate material referenced herein have a particle size as measured by sieve analysis of no greater than about 1000 μm, such as no greater than about 500 μm, such as no greater than about 400 μm, such as no greater than about 350 μm, such as no greater than about 300 μm. In some embodiments, at least 70% by weight of the particles of any particulate material referenced herein have a particle size as measured by sieve analysis of no greater than about 1000 μm, such as no greater than about 500 μm, such as no greater than about 400 μm, such as no greater than about 350 μm, such as no greater than about 300 μm. In some embodiments, at least 80% by weight of the particles of any particulate material referenced herein have a particle size as measured by sieve analysis of no greater than about 1000 μm, such as no greater than about 500 μm, such as no greater than about 400 μm, such as no greater than about 350 μm, such as no greater than about 300 μm. In some embodiments, at least 90% by weight of the particles of any particulate material referenced herein have a particle size as measured by sieve analysis of no greater than about 1000 μm, such as no greater than about 500 μm, such as no greater than about 400 μm, such as no greater than about 350 μm, such as no greater than about 300 μm. In some embodiments, at least 95% by weight of the particles of any particulate material referenced herein have a particle size as measured by sieve analysis of no greater than about 1000 μm, such as no greater than about 500 μm, such as no greater than about 400 μm, such as no greater than about 350 μm, such as no greater than about 300 μm. In some embodiments, at least 99% by weight of the particles of any particulate material referenced herein have a particle size as measured by sieve analysis of no greater than about 1000 μm, such as no greater than about 500 μm, such as no greater than about 400 μm, such as no greater than about 350 μm, such as no greater than about 300 μm. In some embodiments, approximately 100% by weight of the particles of any particulate material referenced herein have a particle size as measured by sieve analysis of no greater than about 1000 μm, such as no greater than about 500 μm, such as no greater than about 400 μm, such as no greater than about 350 μm, such as no greater than about 300 μm.

In some embodiments, at least 50% by weight, such as at least 60% by weight, such as at least 70% by weight, such as at least 80% by weight, such as at least 90% by weight, such as at least 95% by weight, such as at least 99% by weight of the particles of any particulate material referenced herein have a particle size as measured by sieve analysis of from about 0.01 μm to about 1000 μm, such as from about 0.05 μm to about 750 μm, such as from about 0.1 μm to about 500 μm, such as from about 0.25 μm to about 500 μm. In some embodiments, at least 50% by weight, such as at least 60% by weight, such as at least 70% by weight, such as at least 80% by weight, such as at least 90% by weight, such as at least 95% by weight, such as at least 99% by weight of the particles of any particulate material referenced herein have a particle size as measured by sieve analysis of from about 10 μm to about 400 μm, such as from about 50 μm to about 350 μm, such as from about 100 μm to about 350 μm, such as from about 200 μm to about 300 μm.

Preparation of the Composition

The manner by which the various components of the mixture are combined may vary. As such, the overall mixture of various components with e.g., powdered mixture components may be relatively uniform in nature. The components noted above, which may be in liquid or dry solid form, can be admixed in a pretreatment step prior to mixture with any remaining components of the mixture, or simply mixed together with all other liquid or dry ingredients. The various components of the mixture may be contacted, combined, or mixed together using any mixing technique or equipment known in the art. Any mixing method that brings the mixture ingredients into intimate contact can be used, such as a mixing apparatus featuring an impeller or other structure capable of agitation. Examples of mixing equipment include casing drums, conditioning cylinders or drums, liquid spray apparatus, conical-type blenders, ribbon blenders, mixers available as FKM130, FKM600, FKM1200, FKM2000 and FKM3000 from Littleford Day, Inc., Plough Share types of mixer cylinders, Hobart mixers, and the like. See also, for example, the types of methodologies set forth in U.S. Pat. No. 4,148,325 to Solomon et al.; U.S. Pat. No. 6,510,855 to Korte et al.; and U.S. Pat. No. 6,834,654 to Williams, each of which is incorporated herein by reference. Manners and methods for formulating mixtures will be apparent to those skilled in the art. See, for example, the types of methodologies set forth in U.S. Pat. No. 4,148,325 to Solomon et al.; U.S. Pat. No. 6,510,855 to Korte et al.; and U.S. Pat. No. 6,834,654 to Williams, U.S. Pat. No. 4,725,440 to Ridgway et al., and U.S. Pat. No. 6,077,524 to Bolder et al., each of which is incorporated herein by reference.

In some embodiments, the compositions may be prepared such that the composition mixture may be used in a starchless molding process or a starch-based molding process. Example types of molds that may be used in a production process, include, for example, starch molds, starchless molds, pectin molds, plastic tray molds, silicone tray molds, metallic tray molds, neoprene tray molds, and the like.

Configured for Oral Use

Provided herein is a composition configured for oral use. The term "configured for oral use" as used herein means that the composition is provided in a form such that during use, saliva in the mouth of the user causes one or more of the components of the composition (e.g., basic amine, flavoring agents and/or active ingredients) to pass into the mouth of the user. In certain embodiments, the composition is adapted to deliver components to a user through mucous membranes in the user's mouth, the user's digestive system, or both, and, in some instances, said component is a nicotine component or an active ingredient (including, but not limited to, for example, nicotine, a stimulant, vitamin, amino acid, botanical, or a combination thereof) that can be absorbed through the mucous membranes in the mouth or absorbed through the digestive tract when the product is used.

Compositions configured for oral use as described herein may take various forms, including gels, pastilles, gums, chews, melts, tablets, lozenges, granules, powders, and pouches. Gels can be soft or hard. Certain compositions of the disclosure are in the form of solids. Certain compositions can exhibit, for example, one or more of the following characteristics: crispy, granular, chewy, syrupy, pasty, fluffy, smooth, and/or creamy. In certain embodiments, the desired textural property can be selected from the group consisting of adhesiveness, cohesiveness, density, dryness, fracturability, graininess, gumminess, hardness, heaviness, moisture absorption, moisture release, mouthcoating, roughness, slipperiness, smoothness, viscosity, wetness, and combinations thereof.

The compositions of the present disclosure may be dissolvable. As used herein, the terms "dissolve," "dissolving," and "dissolvable" refer to compositions having aqueous-soluble components that interact with moisture in the oral cavity and enter into solution, thereby causing gradual consumption of the composition. According to one aspect, the dissolvable composition is capable of lasting in the user's mouth for a given period of time until it completely dissolves. Dissolution rates can vary over a wide range, from about 1 minute or less to about 60 minutes. For example, fast release compositions typically dissolve and/or release the desired component(s) (e.g., active ingredient, flavor, and the like) in about 2 minutes or less, often about 1 minute or less (e.g., about 50 seconds or less, about 40 seconds or less, about 30 seconds or less, or about 20 seconds or less). Dissolution can occur by any means, such as melting, mechanical disruption (e.g., chewing), enzymatic or other chemical degradation, or by disruption of the interaction between the components of the composition. In other embodiments, the products do not dissolve during the product's residence in the user's mouth.

The compositions as disclosed herein can be formed into a variety of shapes, including pills, tablets, spheres, strips, films, sheets, coins, cubes, beads, ovoids, obloids, cylinders, bean-shaped, sticks, or rods. Cross-sectional shapes of the composition can vary, and example cross-sectional shapes include circles, squares, ovals, rectangles, and the like. Such shapes can be formed in a variety of manners using equipment such as moving belts, nips, extruders, granulation devices, compaction devices, and the like.

Certain compositions configured for oral use are in the form of pastilles. As used herein, the term "pastille" refers to a dissolvable oral composition made by solidifying a liquid or gel composition so that the final composition is a somewhat hardened solid gel. The rigidity of the gel is highly variable. A pastille product may alternatively be referred to as a soft lozenge. In certain embodiments, the pastille products of the disclosure are characterized by sufficient cohesiveness to withstand light chewing action in the oral cavity without rapidly disintegrating. The pastille products of the disclosure typically do not exhibit a highly deformable chewing quality as found in conventional chewing gum.

In some embodiments, the products disclosed herein may be in the form of a dissolvable lozenge product configured for oral use. Example lozenge-type products of the invention have the form of a lozenge, tablet, microtab, or other tablet-type product. See, for example, the types of nicotine-containing lozenges, lozenge formulations, lozenge formats and configurations, lozenge characteristics and techniques for formulating or manufacturing lozenges set forth in U.S. Pat. No. 4,967,773 to Shaw; U.S. Pat. No. 5,110,605 to Acharya; U.S. Pat. No. 5,733,574 to Dam; U.S. Pat. No. 6,280,761 to Santus; U.S. Pat. No. 6,676,959 to Andersson et al.; U.S. Pat. No. 6,248,760 to Wilhelmsen; and U.S. Pat. No. 7,374,779; US Pat. Pub. Nos. 2001/0016593 to Wilhelmsen; 2004/0101543 to Liu et al.; 2006/0120974 to Mcneight; 2008/0020050 to Chau et al.; 2009/0081291 to Gin et al.; and 2010/0004294 to Axelsson et al.; which are incorporated herein by reference.

Lozenge products are generally described as "hard" and are distinguished in this manner from soft lozenges (i.e., pastilles). Hard lozenges are mixtures of sugars and/or carbohydrates in an amorphous state. Although they are made from aqueous syrups, the water, which is initially present, evaporates as the syrup is boiled during processing so that the moisture content in the finished product is very low, such as 0.5% to 1.5% by weight. To obtain lozenges that are hard and not tacky, the temperature of the melt generally must reach the hard crack stage, with an example temperature range of 149° to 154° C.

In some embodiments, the composition can be chewable, meaning the composition has a mild resilience or "bounce" upon chewing, and possesses a desirable degree of malleability. A composition in chewable form may be entirely dissolving or may be in the form of a non-dissolving gum in which only certain components (e.g., active ingredients, flavor, sweetener) dissolve, leaving behind a non-dissolving matrix. Chewable embodiments generally include a binder, such as a natural gum or pectin. In some embodiments, the composition in chewable form comprises pectin and an organic acid, along with one or more sugar alcohols in an amount by weight of at least 50%, based on the total weight of the composition. Generally, the pectin is present in an amount of from about 1 to about 3% by weight, based on the total weight of the composition.

In some embodiments, the composition can be meltable as discussed, for example, in US Patent App. Pub. No. 2012/0037175 to Cantrell et al., incorporated by reference herein in its entirety. As used herein, "melt," "melting," and "meltable" refer to the ability of the composition to change from a solid state to a liquid state. That is, melting occurs when a substance (e.g., a composition as disclosed herein) changes from solid to liquid, usually by the application of heat. The application of heat in regard to a composition as disclosed herein is provided by the internal temperature of a user's mouth. Thus, the term "meltable" refers to a composition that is capable of liquefying in the mouth of the user as the composition changes phase from solid to liquid and is intended to distinguish compositions that merely disintegrate in the oral cavity through loss of cohesiveness within the composition that merely dissolve in the oral cavity as aqueous-soluble components of the composition interact with moisture. Generally, meltable compositions comprise a lipid as described herein above. In some embodiments, the composition in meltable form comprises a lipid in an amount of from about 35 to about 50% by weight, based on the total weight of the composition, and a sugar alcohol in an amount of from about 35 to about 55% by weight, based on the total weight of the composition. In some embodiments, the sugar alcohol is isomalt, erythritol, sorbitol, arabitol, ribitol, maltitol, dulcitol, iditol, mannitol, xylitol, lactitol, or a combination thereof. In some embodiments, the sugar alcohol is isomalt.

In certain embodiments, the composition is in the form of a compressed or molded pellet. Example pellet weights range from about 250 mg to about 1500 mg, such as about 250 mg to about 700 mg, or from about 700 mg to about 1500 mg. The pellet can have any of a variety of shapes, including traditional pill or tablet shapes. Generally, the composition in tablet form comprises a glucose-polysaccharide blend and a sugar alcohol. In some embodiments, the glucose-polysaccharide blend is present in an amount of from about 35 to about 50% by weight, based on the total weight of the composition; and the sugar alcohol is present in an amount of from about 30 to about 45% by weight, based on the total weight of the composition. In some embodiments, the sugar alcohol is isomalt, erythritol, sorbitol, arabitol, ribitol, maltitol, dulcitol, iditol, mannitol, xylitol, lactitol, or a combination thereof. In some embodiments, the sugar alcohol is isomalt.

In one embodiment, the composition of the present disclosure is disposed within a moisture-permeable container (e.g., a water-permeable pouch). The composition enclosed in the pouch may be in any desired form. In certain embodiments, the composition is in granular form. Such compositions in the water-permeable pouch format are typically used by placing one pouch containing the composition in the mouth of a human subject/user. Generally, the pouch is placed somewhere in the oral cavity of the user, for example under the lips, in the same way as moist snuff products are generally used. The pouch preferably is not chewed or swallowed unless the pouch composition or materials are ingestible (e.g., dissolvable or dispersable) as described herein below. Exposure to saliva then causes some of the components of the composition therein (e.g., flavoring agents and/or nicotine) to pass through e.g., the water-permeable pouch and provide the user with flavor and satisfaction, and the user is not required to spit out any portion of the mixture. After about 10 minutes to about 60 minutes, typically about 15 minutes to about 45 minutes of use/enjoyment, substantial amounts of the mixture have been ingested by the human subject, and the pouch may be removed from the mouth of the human subject for disposal.

In some embodiments, oral products provided herein may be in the form of center-filled pastilles or lozenges, for example, such that the interior (or at least a portion) of the product has one or more different organoleptic properties (e.g., texture, mouthfeel, taste, etc.) from the outer surface thereof (or other portion thereof). Such center-filled pastille or lozenge formulations may include a liquid and/or a gel and/or a meltable and/or a chewable and/or a gummy and/or an effervescent center-filling that is surrounded by a harder outer shell that can be associated with pastille-type or lozenge products as described herein. In such embodiments, the center-filling may be described as having less rigidity and/or increased softness compared to the outer shell. In some embodiments, the center-filling may or may not include an active ingredient therein. For example, in some embodiments, both the outer shell and the center-filling formulations may include an active ingredient so as to provide an extended release of the active ingredient therefrom. In some embodiments, at least the outer shell formulation includes a pastille formulation as described herein above. In other embodiments, both the outer shell formulation and the center-filling formulation may comprise a pastille formulation as described herein having similar or different organoleptic properties.

Accordingly, in certain embodiments, the composition as disclosed herein and any other components noted above are combined within a moisture-permeable packet or pouch that acts as a container for use of the composition to provide a pouched product configured for oral use. Certain embodiments of the disclosure will be described with reference to FIG. 1 of the accompanying drawings, and these described embodiments involve snus-type products having an outer pouch and containing a mixture as described herein. As explained in greater detail below, such embodiments are provided by way of example only, and the pouched products of the present disclosure can include the composition in other forms. The mixture/construction of such packets or pouches, such as the container pouch 102 in the embodiment illustrated in FIG. 1, may be varied. Referring to FIG. 1, there is shown a first embodiment of a pouched product 100. The pouched product 100 includes a moisture-permeable container in the form of a pouch 102, which contains a material 104 comprising a composition as described herein.

Suitable packets, pouches or containers of the type used for the manufacture of smokeless tobacco products are available under the tradenames CatchDry, Ettan, General, Granit, Goteborgs Rape, Grovsnus White, Metropol Kaktus, Mocca Anis, Mocca Mint, Mocca Wintergreen, Kicks, Probe, Prince, Skruf and TreAnkrare. The mixture may be contained in pouches and packaged, in a manner and using the types of components used for the manufacture of conventional snus types of products. The pouch provides a liquid-permeable container of a type that may be considered to be similar in character to the mesh-like type of material that is used for the construction of a tea bag. Components of the mixture readily diffuse through the pouch and into the mouth of the user.

Non-limiting examples of suitable types of pouches are set forth in, for example, U.S. Pat. No. 5,167,244 to Kjerstad and U.S. Pat. No. 8,931,493 to Sebastian et al.; as well as US Patent App. Pub. Nos. 2016/0000140 to Sebastian et al.; 2016/0073689 to Sebastian et al.; 2016/0157515 to Chapman et al.; and 2016/0192703 to Sebastian et al., each of which are incorporated herein by reference. Pouches can be provided as individual pouches, or a plurality of pouches (e.g., 2, 4, 5, 10, 12, 15, 20, 25 or 30 pouches) can be connected or linked together (e.g., in an end-to-end manner) such that a single pouch or individual portion can be readily removed for use from a one-piece strand or matrix of pouches.

An example pouch may be manufactured from materials, and in such a manner, such that during use by the user, the pouch undergoes a controlled dispersion or dissolution. Such pouch materials may have the form of a mesh, screen, perforated paper, permeable fabric, or the like. For example, pouch material manufactured from a mesh-like form of rice paper, or perforated rice paper, may dissolve in the mouth of the user. As a result, the pouch and mixture each may undergo complete dispersion within the mouth of the user during normal conditions of use, and hence the pouch and mixture both may be ingested by the user. Other examples of pouch materials may be manufactured using water dispersible film forming materials (e.g., binding agents such as alginates, carboxymethylcellulose, xanthan gum, pullulan, and the like), as well as those materials in combination with materials such as ground cellulosics (e.g., fine particle size wood pulp). Preferred pouch materials, though water dispersible or dissolvable, may be designed and manufactured such that under conditions of normal use, a significant amount of the mixture contents permeate through the pouch material prior to the time that the pouch undergoes loss of its physical integrity. If desired, flavoring ingredients, disintegration aids, and other desired components, may be incorporated within, or applied to, the pouch material.

The amount of material contained within each product unit, for example, a pouch, may vary. In some embodiments, the weight of the composition within each pouch is at least about 50 mg, for example, from about 50 mg to about 1 gram, from about 100 to 800 about mg, or from about 200 to about 700 mg. In some smaller embodiments, the weight of the composition within each pouch may be from about 100 to about 300 mg. For a larger embodiment, the weight of the composition within each pouch may be from about 300 mg to about 700 mg. If desired, other components can be contained within each pouch. For example, at least one flavored strip, piece or sheet of flavored water dispersible or water-soluble material (e.g., a breath-freshening edible film type of material) may be disposed within each pouch along with or without at least one capsule. Such strips or sheets may be folded or crumpled in order to be readily incorporated within the pouch. See, for example, the types of materials and technologies set forth in U.S. Pat. No. 6,887,307 to Scott et al. and U.S. Pat. No. 6,923,981 to Leung et al.; and The EFSA Journal (2004) 85, 1-32; which are incorporated herein by reference.

A pouched product as described herein can be packaged within any suitable inner packaging material and/or outer container. See also, for example, the various types of containers for smokeless types of products that are set forth in U.S. Pat. No. 7,014,039 to Henson et al.; U.S. Pat. No. 7,537,110 to Kutsch et al.; U.S. Pat. No. 7,584,843 to Kutsch et al.; U.S. Pat. No. 8,397,945 to Gelardi et al., D592,956 to Thiellier; D594,154 to Patel et al.; and D625,178 to Bailey et al.; US Pat. Pub. Nos. 2008/0173317 to Robinson et al.;

2009/0014343 to Clark et al.; 2009/0014450 to Bjorkholm; 2009/0250360 to Bellamah et al.; 2009/0266837 to Gelardi et al.; 2009/0223989 to Gelardi; 2009/0230003 to Thiellier; 2010/0084424 to Gelardi; and 2010/0133140 to Bailey et al; 2010/0264157 to Bailey et al.; and 2011/0168712 to Bailey et al. which are incorporated herein by reference.

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

EXAMPLES

Aspects of the present invention are more fully illustrated by the following examples, which are set forth to illustrate certain aspects of the present invention and are not to be construed as limiting thereof.

Example 1. Nicotine-Monomenthyl Succinate Ion Pair Solution (12% Nicotine by Weight)

An ion pair solution was formed by mixing together 72 g of a 25% aqueous solution of nicotine, 28.4 g of monomenthyl succinate, and 49.5 g deionized water. The concentration of the nicotine-monomenthyl succinate ion pair in the solution, expressed as nicotine, was about 12% by weight.

Example 2. Nicotine-Monomenthyl Succinate Ion Pair Solution (18% Nicotine by Weight)

An ion pair solution was formed by mixing together 114.7 g of a 25% aqueous solution of nicotine and 45.3 g of monomenthyl succinate. The concentration of the nicotine monomenthyl succinate ion pair in the solution, expressed as nicotine, was about 18% by weight.

Example 3. Nicotine-Tocopherol Succinate Ion Pair Solution (9% Nicotine by Weight)

An ion pair solution was formed by mixing 72 g of a 25% aqueous solution of nicotine, 58.9 g of tocopherol succinate, and 69 g of propylene glycol. The concentration of the nicotine-tocopherol succinate ion pair in the solution, expressed as nicotine, was about 9% by weight.

Example 4. Additional Nicotine Ion Pair Solutions

Ion pair solutions are formed by mixing a 25% aqueous solution of nicotine with monomenthyl glutarate, bixin, or norbixin following the procedures of Examples 1-3. To enhance solubility of the ion pair in solution, a solubility enhancer may be added, for example, glycerol, propylene glycol, or other appropriate solvents. The concentration of the nicotine-organic acid ion pair in the solution, expressed as nicotine, may vary.

Example 5. Isomalt Syrup Base

An isomalt syrup base was made by combining 1437 g of isomalt powder, 15.2 g of a 75% aqueous solution of maltitol, 21 g of sodium chloride, 75 g of deionized water, and 0.5 g of sucralose, and heating the mixture to 160° C.

Example 6. Lozenges Comprising a Nicotine-Monomenthyl Succinate Ion Pair

An isomalt-based lozenge was prepared by mixing 0.91 g of the ion-paired solution of Example 2 with 154.7 g of the isomalt syrup of Example 5 at a temperature of about 285° F. The hot mixture was poured into a metal mold to provide individual pieces having a weight of about 1.9 g and containing about 2 mg nicotine (on a free base basis) as a nicotine-monomenthyl succinate ion pair. The individual pieces were cooled to room temperature. The lozenges exhibited good clarity. Qualitatively, on oral dissolution, the lozenges exhibited little buccal and throat irritation.

Example 7. Pouched Product Comprising a Nicotine-Tocopherol Succinate Ion Pair An oral pouched product containing a nicotine-tocopherol succinate ion pair composition is prepared according to the formulation of Table 2. Microcrystalline cellulose and salt are blended together. The nicotine tocopherol succinate ion pair solution of Example 3 is combined with a nicotine benzoate ion pair solution (12% nicotine), sweetener, and deionized water. The mixture is combined with the previously prepared microcrystalline cellulose and salt blend to provide the composition. The composition is transferred to a pouch filler, and the oral pouched product fabricated by adding the pouch filler contents into a non-woven fleece and heat sealing the fleece. The final pouched product contains about 494 mg of the composition. Water is added to the pouch, giving a final weight of about 588 mg. The nicotine content of each pouch, in the form of nicotine benzoate and nicotine tocopherol succinate ion pairs, is about 6.0 mg on a free base nicotine basis.

TABLE 2

Oral pouched product composition components and amounts

| Component | % by weight of composition |
|---|---|
| microcrystalline cellulose | 45-70 |
| sodium chloride | 1.5-2 |
| water | 10-12 |
| nicotine tocopherol succinate (9% nicotine) | 9-11 |
| nicotine benzoate (12% nicotine) | 1-2 |
| sodium benzoate | 0.5-1.5 |
| sweetener | 1-3 |
| water (added to final pouch) | 13-19 |

Example 8. Pouched Product Comprising a Nicotine-Monomenthyl Succinate Ion Air An oral pouched product containing a nicotine-monomenthyl succinate ion pair composition is prepared according to the formulation of Table 3. Microcrystalline cellulose and salt are blended together. The nicotine monomenthyl succinate ion pair solution of Example 2 is combined with a nicotine benzoate ion pair solution (12% nicotine), sweetener, and deionized water. The mixture is combined with the previously prepared microcrystalline cellulose and salt blend to provide the composition. The composition is transferred to a pouch filler, and the oral pouched product fabricated by adding the pouch filler contents into a non-woven fleece and heat sealing the fleece. The final pouched product contains about 494 mg of the composition. Water is added to the pouch, giving a final weight of about 588 mg. The nicotine content of each pouch, in the form of nicotine benzoate and nicotine tocopherol succinate ion pairs, is about 6.0 mg on a free base nicotine basis.

TABLE 3

Oral pouched product composition components and amounts

| Component | % by weight of composition |
|---|---|
| microcrystalline cellulose | 45-70 |
| sodium chloride | 1.5-2 |
| water | 10-12 |
| nicotine monomenthyl succinate (18% nicotine) | 1-2 |
| nicotine benzoate (12% nicotine) | 4-8 |
| sodium benzoate | 1-5 |
| sweetener | 1-3 |
| propylene glycol | 0.5-0.7 |
| water (added to final pouch) | 13-19 |

Example 9. Log P Determination of Nicotine-Monomenthyl Succinate Ion Pair

An aqueous ion pair solution of 100 ppm nicotine and two molar equivalents of monomenthyl succinate was prepared and pH adjusted to 6.0. The log of the octanol water partition coefficient (Log P) for the ion paired solution was determined to be 0.86. This positive partition coefficient denotes the resulting ion pair is lipophilic and is therefore expected to provide enhanced absorption when a product including such an ion pair is consumed.

What is claimed is:

1. A composition configured for oral use, the composition comprising:

at least one filler;

a basic amine which is nicotine;

water; and a combination of an organic acid having a log P value from about 3 to about 12 and an alkali metal salt of an organic acid having a log P value from about 3 to about 12, wherein at least a portion of the basic amine is associated with at least a portion of the organic acid and the alkali metal salt thereof, the association in the form of an ion pair between the basic amine and a conjugate base of the organic acid, and wherein the organic acid is a menthyl or tocopherol monoester of a dicarboxylic acid;

wherein the composition is enclosed in a pouch to form a pouched product, the composition optionally being in a granular form.

2. The composition of claim 1, wherein the dicarboxylic acid is malonic acid, succinic acid, glutaric acid, adipic acid, fumaric acid, maleic acid, or a combination thereof.

3. The composition of claim 1, wherein the organic acid is tocopherol succinate, monomenthyl succinate, monomenthyl fumarate, monomenthyl glutarate, or a combination thereof.

4. The composition of claim 1, wherein the composition further comprises a solubility enhancer.

5. The composition of claim 4, wherein the solubility enhancer is glycerol or propylene glycol.

6. The composition of claim 1, comprising from about 0.05, about 0.1, about 1, about 1.5, about 2, or about 5, to about 10, about 15, or about 20 molar equivalents of the organic acid, the alkali metal salt thereof, or the combination thereof, relative to the basic amine, calculated as the amine free base.

7. The composition of claim 1, comprising from about 2 to about 10 molar equivalents of the organic acid, the alkali metal salt thereof, or the combination thereof, relative to the basic amine, calculated as the amine free base.

8. The composition of claim 1, wherein the organic acid further comprises benzoic acid, an alkali metal salt thereof, or a combination thereof.

9. The composition of claim 1, wherein the alkali metal is sodium or potassium.

10. The composition of claim 9, wherein a ratio of the organic acid to the sodium or potassium salt of the organic acid is from about 0.1 to about 10.

11. The composition of claim 1, wherein the pH of the composition is from about 4.0 to about 9.0.

12. The composition of claim 1, wherein the pH of the composition is from about 4.5 to about 7.

13. The composition of claim 1, wherein the pH of the composition is from about 5.5 to about 7.

14. The composition of claim 1, wherein the pH of the composition is from about 4.0 to about 5.5.

15. The composition of claim 1, wherein the pH of the composition is from about 7.0 to about 9.0.

16. The composition of claim 1, wherein the nicotine is present in an amount of from about 0.001 to about 10% by weight of the composition, calculated as the free base and based on the total weight of the composition.

17. The composition of claim 1, wherein the at least one filler comprises a cellulose material.

18. The composition of claim 17, wherein the cellulose material comprises microcrystalline cellulose.

19. The composition of claim 1, wherein the at least one filler further comprises a cellulose derivative in an amount by weight of from about 1% to about 3%, based on the total weight of the composition.

20. The composition of claim 19, wherein the cellulose derivative is hydroxypropylcellulose.

21. The composition of claim 1, comprising:

from about 10 to about 50% of the at least one filler; and from about 5 to about 60% by weight of water, based on the total weight of the composition.

22. The composition of claim 1, further comprising one or more active ingredients, one or more flavoring agents, one or more salts, one or more sweeteners, one or more binding agents, one or more humectants, one or more gums, a tobacco material, or combinations thereof.

23. The composition of claim 1, further comprising one or more active ingredients selected from the group consisting of nutraceuticals, botanicals, stimulants, amino acids, vitamins, and cannabinoids.

24. The composition of claim 1, comprising no more than about 10% by weight of a tobacco material, excluding any nicotine component present, based on the total weight of the composition.

25. The composition of claim 1, wherein the composition is free of tobacco material.

* * * * *